(12) United States Patent
Tsourkas et al.

(10) Patent No.: US 11,123,440 B2
(45) Date of Patent: Sep. 21, 2021

(54) COMPOSITIONS AND METHODS FOR MAKING ANTIBODY CONJUGATES

(71) Applicant: THE TRUSTEES OF THE UNIVERSITY OF PENNSYLVANIA, Philadelphia, PA (US)

(72) Inventors: Andrew Tsourkas, Bryn Mawr, PA (US); James Z. Hui, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/573,757

(22) PCT Filed: May 12, 2016

(86) PCT No.: PCT/US2016/032221
§ 371 (c)(1),
(2) Date: Nov. 13, 2017

(87) PCT Pub. No.: WO2016/183387
PCT Pub. Date: Nov. 17, 2016

(65) Prior Publication Data
US 2018/0344871 A1    Dec. 6, 2018

Related U.S. Application Data

(60) Provisional application No. 62/160,130, filed on May 12, 2015.

(51) Int. Cl.
| | |
|---|---|
| C07K 14/315 | (2006.01) |
| A61K 47/68 | (2017.01) |
| C07K 16/28 | (2006.01) |
| C07K 16/46 | (2006.01) |
| C12N 15/62 | (2006.01) |
| C12N 9/48 | (2006.01) |
| A61K 39/00 | (2006.01) |

(52) U.S. Cl.
CPC ...... *A61K 47/6889* (2017.08); *A61K 47/6851* (2017.08); *C07K 14/315* (2013.01); *C07K 16/2803* (2013.01); *C07K 16/2809* (2013.01); *C07K 16/2887* (2013.01); *C07K 16/468* (2013.01); *C12N 9/48* (2013.01); *C12N 15/62* (2013.01); *C12Y 304/2207* (2013.01); *A61K 2039/572* (2013.01); *C07K 2317/31* (2013.01); *C07K 2317/52* (2013.01); *C07K 2317/622* (2013.01); *C07K 2317/73* (2013.01); *C07K 2317/92* (2013.01); *C07K 2319/20* (2013.01); *C07K 2319/21* (2013.01); *C07K 2319/30* (2013.01); *C07K 2319/60* (2013.01); *C07K 2319/61* (2013.01); *C07K 2319/70* (2013.01); *C07K 2319/705* (2013.01)

(58) Field of Classification Search
CPC ............ A61K 47/6889; A61K 47/6851; A61K 2039/572; C12N 15/62; C12N 9/48; C12Y 304/2207; C07K 16/2887; C07K 16/468; C07K 14/315; C07K 16/2803; C07K 16/2809; C07K 2317/52; C07K 2317/73; C07K 2317/92; C07K 2319/20; C07K 2319/21; C07K 2319/30; C07K 2319/60; C07K 2319/61; C07K 2319/705; C07K 2319/70; C07K 2317/31; C07K 2317/622
See application file for complete search history.

(56) References Cited

U.S. PATENT DOCUMENTS

2014/0249296 A1    9/2014    Ploegh et al.

FOREIGN PATENT DOCUMENTS

WO    WO 2014/145654 A1    9/2014

OTHER PUBLICATIONS

Jung et al., Anal Chem 81: 936-942 (Year: 2009).*
Hui et al..Small 10(16): 3354-3363, Epublished Apr. 14, (Year: 2014).*
Hui et al., Bioconjugate Chemistry 25: 1709-1719 (Year: 2014).*
Rudikoffetal., Proc. Natl. Acad. Sci. USA 79:1979-1983 (Year: 1982).*
Singh et al.,Curr Protein Pept Sci. 18: 1-11 (Year: 2017).*
Hui et al. Optimization of Photoactive Protein Z for Fast and Efficient SiteSpecific Conjugation of Native IgG: Bioconjugate Chemistry, Aug. 27, 2014 (Aug. 27, 2014), vol. 25, pp. 1709-1719. entire document.
Perols at al. "Site-Specific Photoconjugation of Antibodies Using Chemically Synthesized IgG-Binding Domains," Bioconjugate Chemistry, Feb. 12, 2014 (Feb. 12, 2014), vol. 25. pp. 481-488. entire document.
Wagner et al. "Bispecific antibody generated with sortase and click chemistry has broad antiinfluenza virus activity," Proceedings of the National Academy of Sciences, Nov. 25, 2014 (Nov. 25, 2014), vol. iii, No. 47. pp. 16820-16825. entire document.

* cited by examiner

Primary Examiner — Phuong Huynh
(74) Attorney, Agent, or Firm — Mark S. Cohen; Pearl Cohen; Zedek Latzer Baratz LLP

(57) ABSTRACT

The invention relates to antibody conjugates (e.g., a bispecific antibody), drug and nanoparticle compositions and methods and compositions for generating them. This invention further relates to methods of using these compositions for imaging, diagnosing or treating a disease.

18 Claims, 31 Drawing Sheets
Specification includes a Sequence Listing.

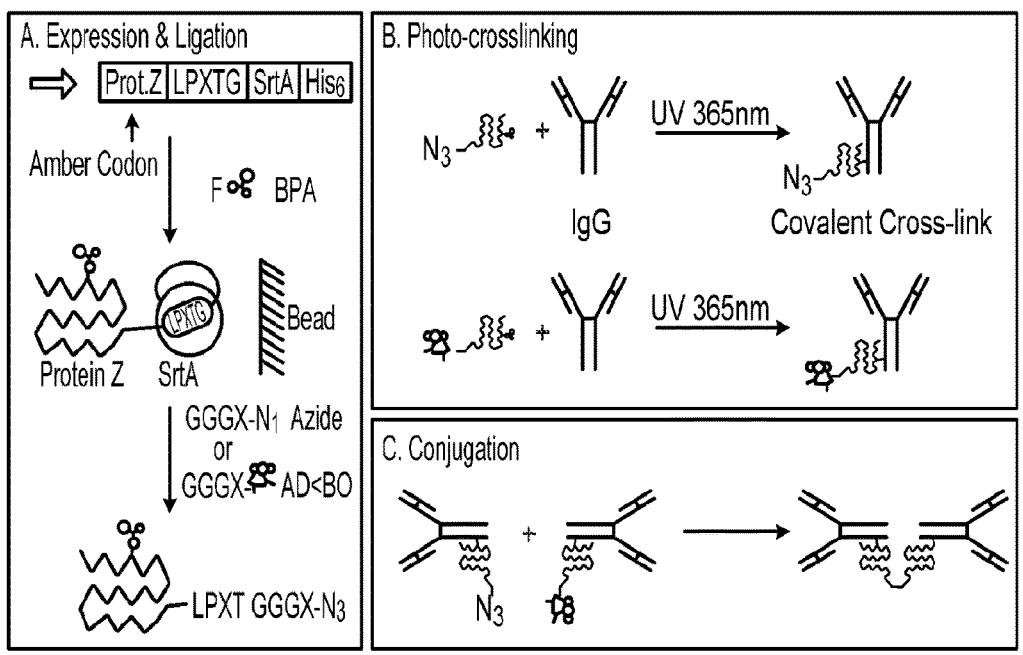
Figure 1
Figure 2
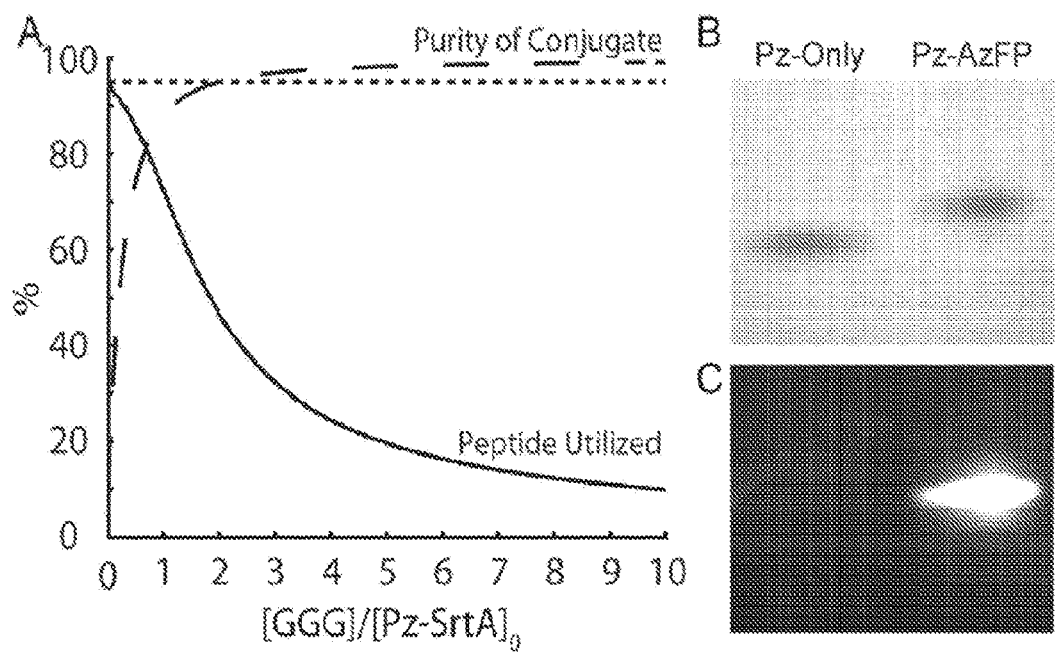

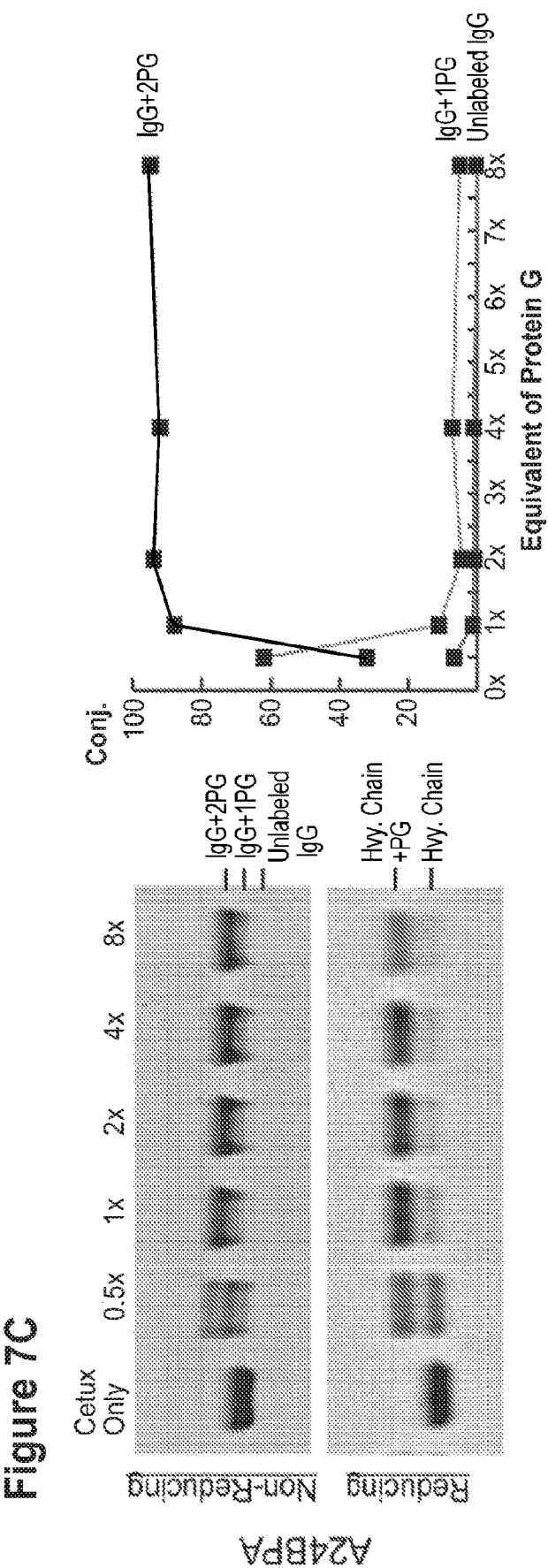

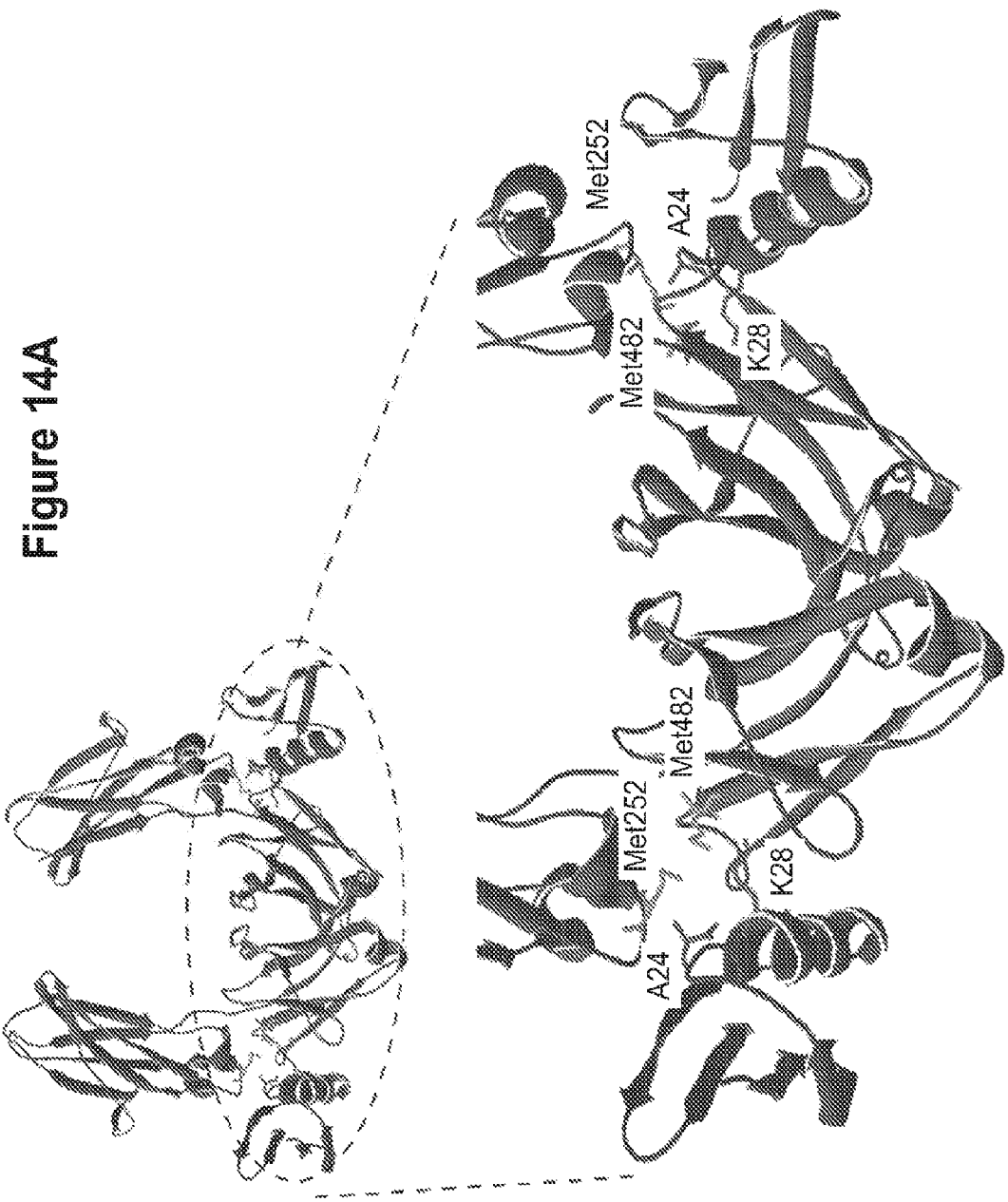

Figure 14B

```
              235                                                              281
hIgG1    L G G P S V F L F P P K P K D T L M I S R T P E V T C V V V D V S H E D P E V K F N W Y V D G
hIgG2    V A G P S V F L F P P K P K D T L M I S R T P E V T C V V V D V S H E D P E V Q F N W Y V D G
hIgG3    L G G P S V F L F P P K P K D T L M I S R T P E V T C V V V D V S H E D P E V Q F K W Y V D G
hIgG4    L G G P S V F L F P P K P K D T L M I S R T P E V T C V V V D V S Q E D P E V Q F N W Y V D G mIgG1    P E V S S V F I F P P K P K D V L T I T L T P K V T C V V V D I S K D D P E V Q F S W F V D D
mIgG2a   L G G P S V F I F P P K I K D V L M I S L S P I V T C V V V D V S E D D P D V Q I S W F V N N
mIgG2b   E G G P S V F I F P P N I K D V L M I S L T P K V T C V V V D V S E D D P D V Q I S W F V N N
mIgG3    L G G P S V F I F P P K P K D A L M I S L T P K V T C V V V D V S E D D P D V H V S W F V D N rIgG1    - - V S S V F I F P P K T K D V L T I T L T P K V T C V V V D I S Q N D P E V R F S W F I D D
rIgG2a   - - V S S V F I F P P K T K D V L T I T L T P K V T C V V V D I S Q N D P E V R F S W F I D D
rIgG2b   L G G P S V F I F P P K P K D I L L I S Q N A K V T C V V V D V S E E D P D V Q F S W F V N N
rIgG2c   L G R P S V F I F P P K P K D I L M I T L T P K V T C V V V D V S E E D P D V Q F S W F V D N rbIgG1   L G G P S V F I F P P K P K D T L M I S R T P E V T C V V V D V S Q D D P E V Q F T W Y I N N
hmIgG1   L G G P S V F I F P P K P K D V L M I S L T P K I T C V V V D V S E E D P D V Q F N W Y V N N
```

Figure 14C

| | 413 | | | | | | | | | | | | | | | | | | | | | | | | | | | | | | | | | | 447 |
|---|---|---|---|---|---|---|---|---|---|---|---|---|---|---|---|---|---|---|---|---|---|---|---|---|---|---|---|---|---|---|---|---|---|---|---|
| hIgG1   | D | K | S | R | W | Q | Q | G | N | V | F | S | C | S | V | M | H | E | A | L | H | N | H | Y | T | Q | K | S | L | S | L | S | P | G | K |
| hIgG2   | D | K | S | R | W | Q | Q | G | N | V | F | S | C | S | V | M | H | E | A | L | H | N | H | Y | T | Q | K | S | L | S | L | S | P | G | K |
| hIgG3   | D | K | S | R | W | Q | Q | G | N | I | F | S | C | S | V | M | H | E | A | L | H | N | R | F | T | Q | K | S | L | S | L | S | P | G | K |
| hIgG4   | D | K | S | R | W | Q | E | G | N | V | F | S | C | S | V | M | H | E | A | L | H | N | H | Y | T | Q | K | S | L | S | L | S | L | G | K |
| mIgG1   | Q | K | S | N | W | E | A | G | N | T | F | T | C | S | V | L | H | E | G | L | H | N | H | H | T | E | K | S | L | S | H | S | P | G | K |
| mIgG2a  | E | K | K | N | W | V | E | K | G | N | Y | F | S | C | S | V | V | H | E | G | L | H | N | H | H | T | T | K | S | F | S | R | T | P | G | L |
| mIgG2b  | K | T | S | K | W | E | K | T | D | S | F | S | C | N | V | R | H | E | G | L | K | N | Y | Y | L | K | K | T | I | S | R | S | P | G | K |
| mIgG3   | D | T | D | S | W | L | Q | G | E | I | F | T | C | S | V | V | H | E | A | L | H | N | H | H | T | Q | K | N | L | S | R | S | P | E | L |
| rIgG1   | K | K | E | K | W | Q | Q | G | N | T | F | T | C | S | V | L | H | E | G | L | H | N | H | H | T | E | K | S | L | S | H | S | P | G | K |
| rIgG2a  | K | K | E | K | W | Q | Q | G | N | T | F | T | C | S | V | L | H | E | G | L | H | N | H | H | T | E | K | S | L | S | R | S | P | G | K |
| rIgG2b  | E | R | S | R | W | D | D | S | R | A | P | F | V | C | S | V | V | H | E | G | L | H | N | H | H | T | E | K | S | L | S | R | S | P | G | K |
| rIgG2c  | D | T | D | S | W | M | R | G | D | I | Y | T | C | S | V | V | H | E | A | L | H | N | H | H | T | Q | K | N | L | S | R | S | P | G | K |
| rbIgG1  | P | T | S | E | W | Q | R | G | D | V | F | T | C | S | V | I | H | E | A | L | H | N | H | Y | T | Q | K | S | I | S | R | S | P | G | K |
| hmIgG1  | P | K | S | R | W | D | Q | G | D | S | F | T | C | S | V | I | H | E | A | L | H | N | H | M | T | K | T | I | K | T | I | R | S | L | G | N |

Figure 19
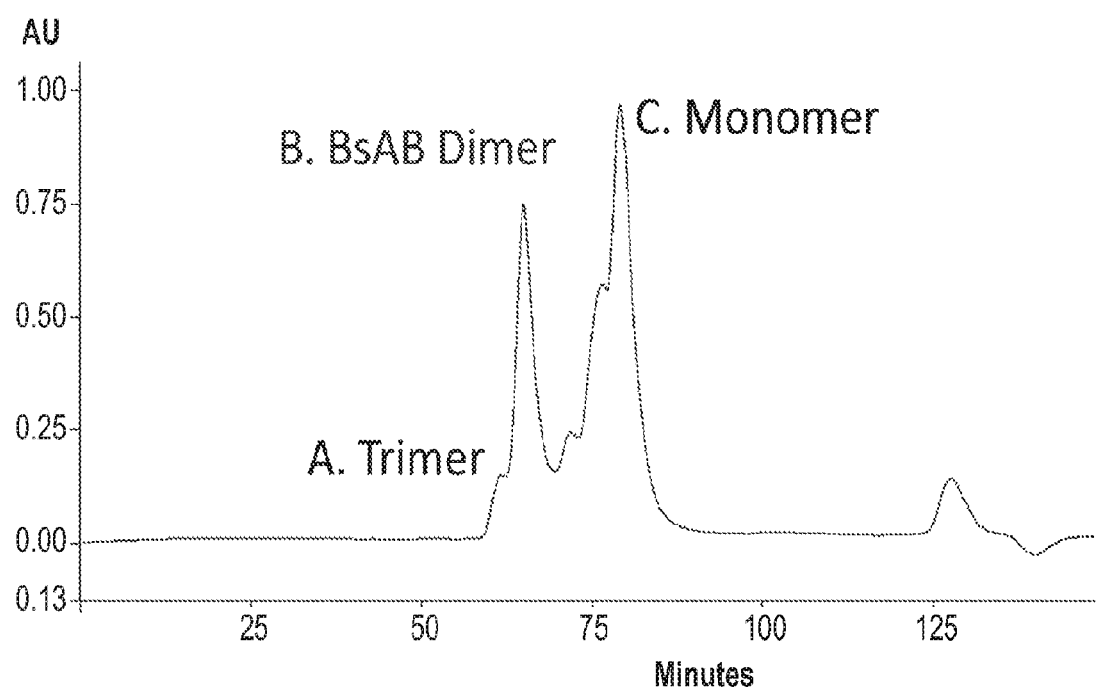
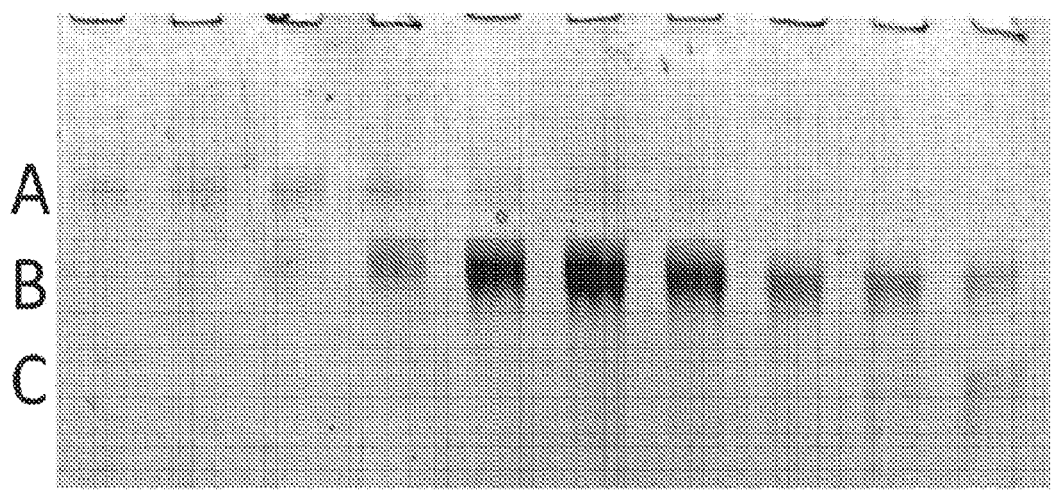

1. OKT3 XL L17-TAM-TCO
2. Click product of 1& 3
3. Rituximab XL K35-FAM-Tetrazine Reducing gel
1. L17-K28 3uL XL Cetux 0.3 + OKT3 0.3
2. L17-K28 6uL XL Cetux 0.3 + OKT3 0.3
3. L17-K28 12uL XL Cetux 0.3 + OKT3 0.3
4. L17-K28 12 XL Cetux 0.3
5. L17-K28 12 XL OKT3 0.3

Non-reducing gel
1. L17-K28 3uL XL Cetux 0.3 + OKT3 0.3
2. L17-K28 6uL XL Cetux 0.3 + OKT3 0.3
3. L17-K28 12uL XL Cetux 0.3 + OKT3 0.3
4. L17-K28 12uL XL Cetux 0.3
5. L17-K28 12uL XL OKT3 0.3

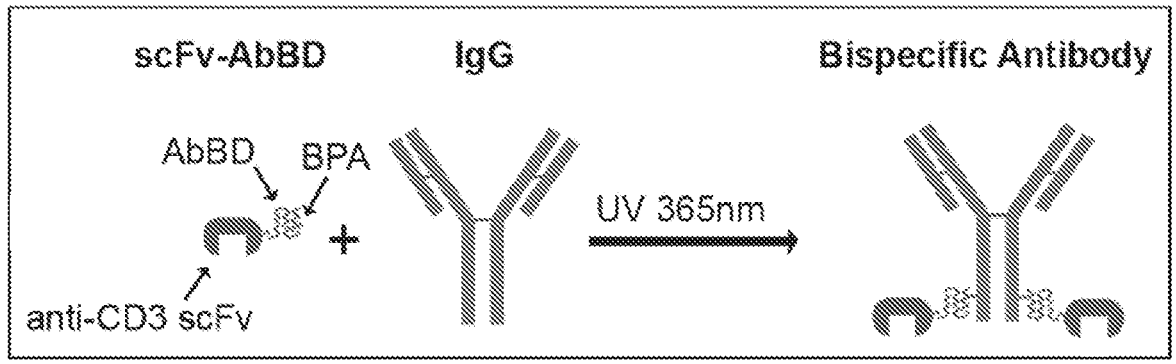
Figure 24
Figure 25
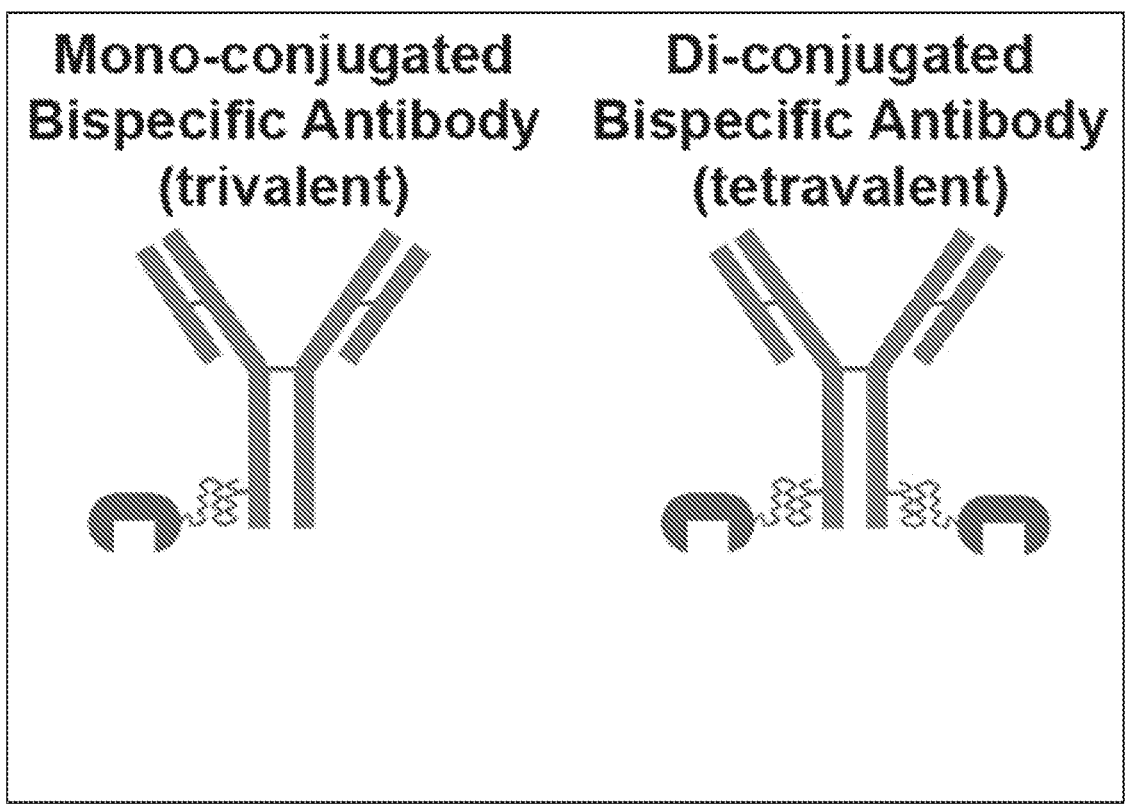

```
                            SEQUENCE LISTING

<160> NUMBER OF SEQ ID NOS: 16

<210> SEQ ID NO 1
<211> LENGTH: 61
<212> TYPE: PRT
<213> ORGANISM: Staphylococcal aureus

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Met Arg Met
    50                  55                  60

<210> SEQ ID NO 2
<211> LENGTH: 56
<212> TYPE: PRT
<213> ORGANISM: Staphylococcal aureus

<400> SEQUENCE: 2

Met Thr Phe Lys Leu Ile Ile Asn Gly Lys Thr Leu Lys Gly Glu Ile
1               5                   10                  15

Thr Ile Glu Ala Val Asp Ala Ala Glu Ala Glu Lys Ile Phe Lys Gln
            20                  25                  30

Tyr Ala Asn Asp Tyr Gly Ile Asp Gly Glu Trp Thr Tyr Asp Asp Ala
        35                  40                  45

Thr Lys Thr Phe Thr Val Thr Glu
    50                  55

<210> SEQ ID NO 3
<211> LENGTH: 47
<212> TYPE: PRT
<213> ORGANISM: Homo Sapiens

<400> SEQUENCE: 3

Leu Gly Gly Pro Ser Val Phe Leu Phe Pro Pro Lys Pro Lys Asp Thr
1               5                   10                  15

Leu Met Ile Ser Arg Thr Pro Glu Val Thr Cys Val Val Val Asp Val
            20                  25                  30

Ser His Glu Asp Pro Glu Val Lys Phe Asn Trp Tyr Val Asp Gly
        35                  40                  45

<210> SEQ ID NO 4
<211> LENGTH: 47
<212> TYPE: PRT
<213> ORGANISM: Homo Sapiens

<400> SEQUENCE: 4

Val Ala Gly Pro Ser Val Phe Leu Phe Pro Pro Lys Pro Lys Asp Thr
1               5                   10                  15
```

-continued

```
Leu Met Ile Ser Arg Thr Pro Glu Val Thr Cys Val Val Asp Val
            20                  25                  30

Ser His Glu Asp Pro Glu Val Gln Phe Asn Trp Tyr Val Asp Gly
        35                  40                  45

<210> SEQ ID NO 5
<211> LENGTH: 47
<212> TYPE: PRT
<213> ORGANISM: Homo Sapiens

<400> SEQUENCE: 5

Leu Gly Gly Pro Ser Val Phe Leu Phe Pro Pro Lys Pro Lys Asp Thr
1               5                  10                  15

Leu Met Ile Ser Arg Thr Pro Glu Val Thr Cys Val Val Asp Val
            20                  25                  30

Ser His Glu Asp Pro Glu Val Gln Phe Lys Trp Tyr Val Asp Gly
        35                  40                  45

<210> SEQ ID NO 6
<211> LENGTH: 47
<212> TYPE: PRT
<213> ORGANISM: Homo Sapiens

<400> SEQUENCE: 6

Leu Gly Gly Pro Ser Val Phe Leu Phe Pro Pro Lys Pro Lys Asp Thr
1               5                  10                  15

Leu Met Ile Ser Arg Thr Pro Glu Val Thr Cys Val Val Asp Val
            20                  25                  30

Ser Gln Glu Asp Pro Glu Val Gln Phe Asn Trp Tyr Val Asp Gly
        35                  40                  45

<210> SEQ ID NO 7
<211> LENGTH: 47
<212> TYPE: PRT
<213> ORGANISM: Mus Musculus

<400> SEQUENCE: 7

Pro Glu Val Ser Ser Val Phe Ile Phe Pro Pro Lys Pro Lys Asp Val
1               5                  10                  15

Leu Thr Ile Thr Leu Thr Pro Lys Val Thr Cys Val Val Asp Ile
            20                  25                  30

Ser Lys Asp Asp Pro Glu Val Gln Phe Ser Trp Phe Val Asp Asp
        35                  40                  45

<210> SEQ ID NO 8
<211> LENGTH: 47
<212> TYPE: PRT
<213> ORGANISM: Mus Musculus

<400> SEQUENCE: 8

Leu Gly Gly Pro Ser Val Phe Ile Phe Pro Pro Lys Ile Lys Asp Val
1               5                  10                  15

Leu Met Ile Ser Leu Ser Pro Ile Val Thr Cys Val Val Asp Val
            20                  25                  30

Ser Glu Asp Asp Pro Asp Val Gln Ile Ser Trp Phe Val Asn Asn
        35                  40                  45

<210> SEQ ID NO 9
<211> LENGTH: 47
<212> TYPE: PRT
```

<213> ORGANISM: Mus Musculus

<400> SEQUENCE: 9

Glu Gly Gly Pro Ser Val Phe Ile Phe Pro Asn Ile Lys Asp Val
1               5                   10                  15

Leu Met Ile Ser Leu Thr Pro Lys Val Thr Cys Val Val Asp Val
            20                  25                  30

Ser Glu Asp Asp Pro Asp Val Gln Ile Ser Trp Phe Val Asn Asn
        35                  40                  45

<210> SEQ ID NO 10
<211> LENGTH: 47
<212> TYPE: PRT
<213> ORGANISM: Mus Musculus

<400> SEQUENCE: 10

Leu Gly Gly Pro Ser Val Phe Ile Phe Pro Lys Pro Lys Asp Ala
1               5                   10                  15

Leu Met Ile Ser Leu Thr Pro Lys Val Thr Cys Val Val Asp Val
            20                  25                  30

Ser Glu Asp Asp Pro Asp Val His Val Ser Trp Phe Val Asp Asn
        35                  40                  45

<210> SEQ ID NO 11
<211> LENGTH: 45
<212> TYPE: PRT
<213> ORGANISM: Rattus Norvegicus

<400> SEQUENCE: 11

Val Ser Ser Val Phe Ile Phe Pro Pro Lys Thr Lys Asp Val Leu Thr
1               5                   10                  15

Ile Thr Leu Thr Pro Lys Val Thr Cys Val Val Val Asp Ile Ser Gln
            20                  25                  30

Asn Asp Pro Glu Val Arg Phe Ser Trp Phe Ile Asp Asp
        35                  40                  45

<210> SEQ ID NO 12
<211> LENGTH: 45
<212> TYPE: PRT
<213> ORGANISM: Rattus Norvegicus

<400> SEQUENCE: 12

Val Ser Ser Val Phe Ile Phe Pro Pro Lys Thr Lys Asp Val Leu Thr
1               5                   10                  15

Ile Thr Leu Thr Pro Lys Val Thr Cys Val Val Val Asp Ile Ser Gln
            20                  25                  30

Asn Asp Pro Glu Val Arg Phe Ser Trp Phe Ile Asp Asp
        35                  40                  45

<210> SEQ ID NO 13
<211> LENGTH: 47
<212> TYPE: PRT
<213> ORGANISM: Rattus Norvegicus

<400> SEQUENCE: 13

Leu Gly Gly Pro Ser Val Phe Ile Phe Pro Lys Pro Lys Asp Ile
1               5                   10                  15

Leu Leu Ile Ser Gln Asn Ala Lys Val Thr Cys Val Val Val Asp Val
            20                  25                  30

Ser Glu Glu Glu Pro Asp Val Gln Phe Ser Trp Phe Val Asn Asn

```
                    35                  40                  45

<210> SEQ ID NO 14
<211> LENGTH: 47
<212> TYPE: PRT
<213> ORGANISM: Rattus Norvegicus

<400> SEQUENCE: 14

Leu Gly Arg Pro Ser Val Phe Ile Phe Pro Pro Lys Pro Lys Asp Ile
1               5                   10                  15

Leu Met Ile Thr Leu Thr Pro Lys Val Thr Cys Val Val Val Asp Val
            20                  25                  30

Ser Glu Glu Glu Pro Asp Val Gln Phe Ser Trp Phe Val Asp Asn
            35                  40                  45

<210> SEQ ID NO 15
<211> LENGTH: 47
<212> TYPE: PRT
<213> ORGANISM: Oryctolagus cuniculus

<400> SEQUENCE: 15

Leu Gly Gly Pro Ser Val Phe Ile Phe Pro Pro Lys Pro Lys Asp Thr
1               5                   10                  15

Leu Met Ile Ser Arg Thr Pro Glu Val Thr Cys Val Val Val Asp Val
            20                  25                  30

Ser Gln Asp Asp Pro Glu Val Gln Phe Thr Trp Tyr Ile Asn Asn
            35                  40                  45

<210> SEQ ID NO 16
<211> LENGTH: 47
<212> TYPE: PRT
<213> ORGANISM: Mesocrictus auratus

<400> SEQUENCE: 16

Leu Gly Gly Pro Ser Val Phe Ile Phe Pro Pro Lys Pro Lys Asp Val
1               5                   10                  15

Leu Met Ile Ser Leu Thr Pro Lys Ile Thr Cys Val Val Val Asp Val
            20                  25                  30

Ser Glu Glu Glu Pro Asp Val Gln Phe Asn Trp Tyr Val Asn Asn
            35                  40                  45
```

COMPOSITIONS AND METHODS FOR MAKING ANTIBODY CONJUGATES

CROSS-REFERENCE TO RELATED APPLICATIONS

This application is a National Phase Application of PCT International Application No. PCT/US16/32221, filed May 12, 2016, which claims priority to and the benefit of U.S. Provisional Patent Application 62/160,130, filed May 12, 2015, each of which is incorporated by reference herein in its entirety.

GOVERNMENT INTEREST STATEMENT

This invention was supported by Grant Numbers R01EB012065, R01CA157766, R21EB018863, and R21CA187657 from the National Institutes of Health. The United States government has certain rights in the invention.

FIELD OF THE INVENTION

The invention relates to antibody conjugates (e.g., a bispecific antibody), drug and nanoparticle compositions and methods and compositions for generating them. This invention further relates to methods of using these compositions for imaging, diagnosing or treating a disease, such as cancer.

BACKGROUND OF THE INVENTION

Bispecific antibodies have emerged as a promising cancer treatment, with a growing list of encouraging clinical results. For example, blinatumomab, a murine anti-human CD3× anti-human CD19 bispecific antibody has produced clinical remission in precursor B cell acute lymphoblastic leukemia (B-ALL) patients at thousands times lower dosage than conventional antibody therapies, such as rituximab (anti-human CD20). These findings have spurred a great deal of interest and growth in the field, with particular attention being focused on developing new methodologies to generate bispecific antibodies (e.g., Triomabs, BiTEs, Dock and Lock, etc.) in high yields and purity.

Despite continual progress, current bispecific antibody technologies still require a tremendous amount of antibody engineering and cloning up front to generate even a single functional product, which can be time consuming and challenging. Technologies utilizing scFv's (single chain variable fragments) are also faced with concerns over functionality, solubility, stability, avidity, and pharmacokinetics. Adding to the challenges in producing bispecific antibodies is an incomplete understanding of their modes of action. For example, not all anti-CD3 antibodies work equally well to trigger T-cell activation. Given these uncertainties and the high cost and time required for production, a methodology that allows bispecific antibodies to be rapidly produced without the need for antibody engineering and cloning would be cost-effective, significantly increase throughput, and ultimately lead to a deeper understanding of the underlying biological mechanisms that lead to improved therapeutic efficacy.

Accordingly, there exists a need for improved compositions and methods for making bispecific antibodies and other complex antibody formats.

In some diagnostic and therapeutic applications, antibodies must be conjugated onto a surface (e.g., nanoparticles and microplates) or labeled with a chemical or biological moiety; however, most conventional bioconjugation techniques (e.g., EDC-NHS) exhibit low crosslinking efficiencies and/or hinder functionality due to non-site-specific antibody labeling.

For applications that require antibody immobilization onto surfaces, conventional bioconjugation methods also result in random antibody orientation. This lack of control can result in heteregenous samples, poor reproducibility, and reduced antibody functionality/efficacy. Site-specific conjugation of antibodies has been shown to result in improved antibody functionality/efficacy. Further, the ability to control the orientation of antibodies on surfaces offer advantages in terms of sensitivity, stability and longevity. Unfortunately, most current site-specific antibody conjugation methods require protein engineering (e.g., cysteine handles), which can be technically challenging, time consuming, and costly.

Therefore, there is a need for a simple, rapid, and efficient approach to site-specifically and covalently label IgG with chemical and biological moeities and to control the orientation of antibodies immobilized on surfaces.

SUMMARY OF THE INVENTION

In one aspect, the invention provides a conjugate composition comprising a protein that comprises an antibody-binding domain (AbBD) operably linked to a photoreactive amino acid, wherein said protein is operably linked to an antibody or a fragment thereof. In an exemplary embodiment, the photoreactive amino acid is benzoylphenylalaine (BPA). In another exemplary embodiment, the antibody-binding domain is a domain of protein G (e.g., HTB1).

The invention encompasses all types of antibodies. In a particular embodiment, the invention provides a method to site-specifically label an antibody with a chemical or biological moiety. In one aspect, the invention provides a method to site-specifically attach an antibody onto a surface. In another aspect, the invention provides a method of producing a bispecific antibody from a first antibody or antigen-binding fragment and a second antibody or antigen-binding fragment, the methods comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) site-specifically linking the second antibody or antigen-binding fragment to a second adapter comprising a second antibody binding domain (AbBD) attached to or modified with a second member of the binding pair to form a second adapter-antibody conjugate; and (c) combining the first and second adapter-antibody conjugates under conditions where the first and second members of the binding pair bind to each other to form a bispecific antibody.

In another aspect, the invention provides a method of producing a bispecific antibody from a first antibody or antigen-binding fragment and a second antibody or antigen-binding fragment, the method comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) combining the first adapter-antibody conjugate with a second adapter comprising a second antibody binding domain (AbBD) attached to or modified with a second member of the binding pair under conditions where the first and second members of the binding pair bind to each other; and (c) site-specifically linking the second antibody or antigen-binding fragment to the second adapter to form a bispecific antibody.

In another aspect, the invention provides a method of producing a bispecific antibody from a first antibody or antigen-binding fragment and a second antibody or antigen-binding fragment, the method comprising the steps of (a) combining a first adapter comprising a first antibody binding domain (AbBD) attached to or modified with a first member of a binding pair and a second adapter comprising a second antibody binding domain (AbBD) attached to or modified with a second member of the binding pair under conditions where the first and second members of the binding pair bind to each other; (b) site-specifically linking the first antibody or antigen-binding fragment to the first adapter; and (c) site-specifically linking the second antibody or antigen-binding fragment to the second adapter to form a bispecific antibody.

In another aspect, the invention provides a method of producing a bispecific antibody from a first antibody or antigen-binding fragment and a second antibody or antigen-binding fragment, the method comprising the steps of (a) providing an adapter comprising a first antibody binding domain (AbBD) fused to a second antibody binding domain (AbBD); (b) site-specifically linking the first antibody or antigen-binding fragment to the first AbBD; and (c) site-specifically linking the second antibody or antigen-binding fragment to the second AbBD to form a bispecific antibody.

In another aspect, the invention provides a method of producing a bispecific antibody from a first antibody or antigen-binding fragment and a second antibody or antigen-binding fragment, the method comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) site-specifically attaching, modifying, or fusing a second antibody, antigen-binding fragment, or targeting ligand (e.g. aptamer) with a second member of the binding pair; and (c) combining the first adapter-antibody conjugate and the second antibody, antigen-binding fragment, or targeting ligand under conditions where the first and second members of the binding pair bind to each other to form a bispecific antibody.

In another aspect, the invention provides a method of producing a bispecific antibody from a first antibody or antigen-binding fragment and a second antibody or antigen-binding fragment, the methods comprising the steps of (a) site-specifically linking the first antibody or antigen-binding fragment to a first adapter comprising an antibody binding domain (AbBD) attached to or modified with a first member of a binding pair to form an adapter-antibody conjugate; (b) providing an antibody conjugate comprising the second antibody or antigen-binding fragment attached to or modified with a second member of the binding pair; and (c) combining the adapter-antibody conjugate and antibody conjugate under conditions where the first and second members of the binding pair bind to each other to form a bispecific antibody.

In another aspect, the invention provides a method of producing a bispecific antibody from a first antibody or antigen-binding fragment and an antibody-adapter fusion comprising a second antibody or antigen-binding fragment fused to an adapter comprising an antibody binding domain (AbBD), the method comprising: site-specifically linking the first antibody or antigen-binding fragment to the antibody-adapter.

Also provided herein are bispecific antibodies produced according to the foregoing methods.

In another aspect, the invention provides a conjugate molecule or adapter comprising a protein, such as a Protein G HTB1 domain or Protein Z domain, having one or more amino acids or amino acid modifications that are adapted to specifically bind and crosslink to an immunoglobulin. In another aspect, provided herein is a conjugate molecule or adapter comprising a first antibody binding domain (AbBD) fused to a second antibody binding domain (AbBD), wherein the first AbBD has one or more amino acids or amino acid modifications that are adapted to specifically bind and crosslink to a first immunoglobulin and wherein the second AbBD has one or more amino acids or amino acid modifications that are adapted to specifically bind and crosslink to a second immunoglobulin.

Also provided herein are nucleic acids and vectors that encode the foregoing adapters. Further provided herein are cells that express the foregoing adapters.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1. Schematic of one method for the production of bispecific antibodies. (A) Protein Z is produced in an entirely recombinant manner. This is achieved by using *E. coli* that have been engineered to incorporate the unnatural amino acid, BPA, into proteins during translation. A sortase-mediated Expressed Protein Ligation (EPL) technique can be used to ligate peptides to the carboxy-terminus of recombinant proteins during the affinity purification process. This sortase-mediated EPL technique is described in greater detail in U.S. Appl. No. 61/799,379 (filed Mar. 15, 2013) and in PCT Appl. No. PCT/US2014/030208 entitled "Sortase-Mediated Protein Purification And Ligation" (filed Mar. 17, 2014), both of which are hereby incorporated in their entirety. A crosslinking group (azide, alkyne, biotin, maleimide, etc.) is included on this peptide. (B) Protein Z-conjugates can be photocrosslinked to each IgG. (C) Azide-modified IgG-Protein Z-peptide conjugates can be efficiently conjugated to ADIBO-modified IgG-Protein Z-peptide conjugates to form bispecific antibodies.

FIG. 2. (A) Plot of STEPL-ligation efficiency and the % of the glycine peptide (GGG) utilized, relative to the amount of expressed protein Z (Pz)-SrtA on the affinity column. (B) SDS-PAGE of unmodified Pz and Pz-conjugate. Here, Pz is ligated to a peptide labeled with a fluorophore and azide. (C) Fluorescent image of the gel.

FIG. 14. (FIG. 14A) Model of Protein G binding to Fc (1FCC), and (FIGS. 14B-14C) IgG sequence alignment.

FIG. 19. Easy purification of bispecific antibody dimers from monomers and multimers.

FIG. 24. Schematic describing method for rapid production of bispecific antibodies. An anti-CD3 scFv is fused to a photoreactive antibody-binding domain (AbBD). Administration of non-damaging long-wavelength UV light allows for covalent attachment of the fusion protein to the Fc-region of IgG.

FIG. 25. Schematic of mono-conjugated and di-conjugated bispecific antibodies.

DETAILED DESCRIPTION OF THE INVENTION

Figure 3:
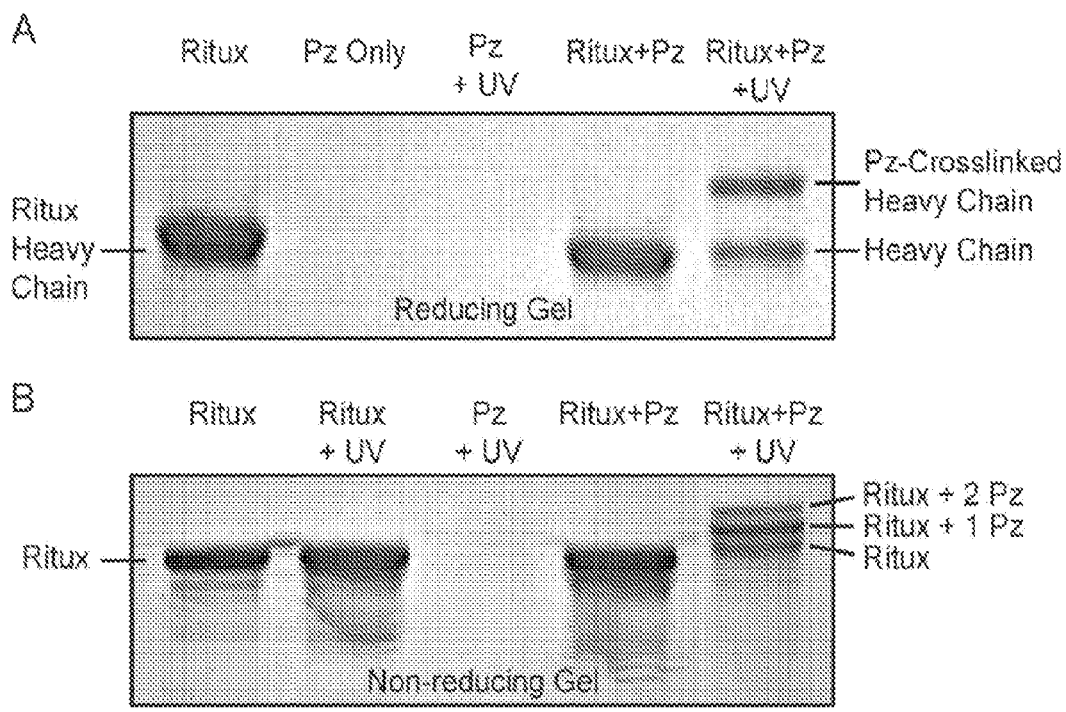
FIG. 3. Protein Z and Rituximab (Ritux) samples with and without UV crosslinking were run on a (A) reducing SDS-PAGE gel and a (B) non-reducing gel.
Figure 4:
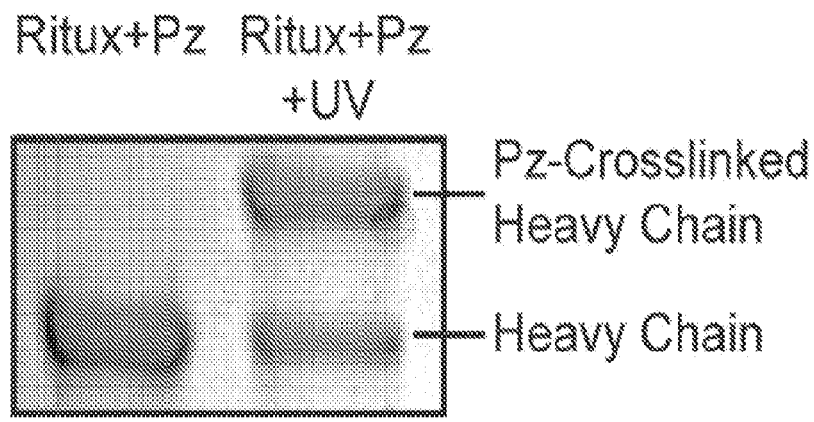
FIG. 4. Reducing SDS-PAGE of Protein Z and Rituximab (Ritux) with and without UV crosslinking.

The invention provides antibody conjugate (e.g., a bispecific antibody), drug and nanoparticle compositions and methods and compositions for generating them. This invention further provides methods of using these compositions for imaging, diagnosing or treating a disease, such as cancer.

In one aspect, provided herein is a conjugate composition comprising a protein that comprises an antibody-binding domain (AbBD) operably linked to a photoreactive amino acid, wherein said protein is operably linked to an antibody or a fragment thereof.

The invention encompasses all types of antibodies. In a particular embodiment, the invention provides a method to site-specifically label an antibody with a chemical or biological moiety. In one aspect, the invention provides a method to site-specifically attach an antibody onto a surface. In another aspect, the invention provides a method of producing a bispecific antibody The inventors of this application have developed facile methods for the efficient production of bispecific antibodies from full-length unmodified IgG, without the need for antibody engineering, cloning, or modifications. The bispecific antibodies can be produced with high purity within just a few hours. Several benefits of working with intact IgG are that they are stable, can be produced in high yield, offer high-avidity bivalent binding, and are expected to maintain Fc-effector functions, including antibody dependent cell-mediated cytotoxicity (ADCC) and complement-dependent cytotoxicity (CDC).

In another aspect, provided herein is a method of producing a bispecific antibody from a first antibody or antigen-binding fragment and a second antibody or antigen-binding fragment, the method comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) site-specifically linking the second antibody or antigen-binding fragment to a second adapter comprising a second antibody binding domain (AbBD) attached to or modified with a second member of the binding pair to form a second adapter-antibody conjugate; and (c) combining the first and second adapter-antibody conjugates under conditions where the first and second members of the binding pair bind to each other to form a bispecific antibody.

In another aspect, provided herein is a method of producing a bispecific antibody from a first antibody or antigen-binding fragment and a second antibody or antigen-binding fragment, the method comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) combining the first adapter-antibody conjugate with a second adapter comprising a second antibody binding domain (AbBD) attached to or modified with a second member of the binding pair under conditions where the first and second members of the binding pair bind to each other; and (c) site-specifically linking the second antibody or antigen-binding fragment to the second adapter to form a bispecific antibody.

In another aspect, provided herein is a method of producing a bispecific antibody from a first antibody or antigen-binding fragment and a second antibody or antigen-binding fragment, the method comprising the steps of (a) combining a first adapter comprising a first antibody binding domain (AbBD) attached to or modified with a first member of a binding pair and a second adapter comprising a second antibody binding domain (AbBD) attached to or modified with a second member of the binding pair under conditions where the first and second members of the binding pair bind to each other; (b) site-specifically linking the first antibody or antigen-binding fragment to the first adapter; and (c) site-specifically linking the second antibody or antigen-binding fragment to the second adapter to form a bispecific antibody. In some embodiments, steps (b) and (c) are performed simultaneously. In some embodiments, steps (b) and (c) are performed sequentially.

In another aspect, provided herein is a method of producing a bispecific antibody from a first antibody or antigen-binding fragment and a second antibody or antigen-binding fragment, the method comprising the steps of (a) providing an adapter comprising a first antibody binding domain (AbBD) fused to a second antibody binding domain (AbBD); (b) site-specifically linking the first antibody or antigen-binding fragment to the first AbBD; and (c) site-specifically linking the second antibody or antigen-binding fragment to the second AbBD to form a bispecific antibody. In some embodiments, steps (b) and (c) are performed simultaneously. In some embodiments, steps (b) and (c) are performed sequentially.

In another aspect, provided herein is a method of producing a bispecific antibody from a first antibody or antigen-binding fragment and a second antibody or antigen-binding fragment, the method comprising the steps of (a) site-specifically linking the first antibody or antigen-binding fragment to a first adapter comprising a first antibody binding domain (AbBD) attached to or modified with a first member of a binding pair to form a first adapter-antibody conjugate; (b) site-specifically attaching, modifying, or fusing a second antibody, antigen-binding fragment, or targeting ligand (e.g. aptamer) with a second member of the binding pair; and (c) combining the first adapter-antibody conjugate and the second antibody, antigen-binding fragment, or targeting ligand under conditions where the first and second members of the binding pair bind to each other to form a bispecific antibody. In some embodiments, the first adapter and the second antibody, antigen-binding fragment, or targeting ligand are combined first, then the first antibody or antigen binding domain is site-specifically linked to the first adapter.

In another aspect, provided herein is a method of producing a bispecific antibody from a first antibody or antigen-binding fragment and a second antibody or antigen-binding fragment, the method comprising the steps of (a) site-specifically linking the first antibody or antigen-binding fragment to a first adapter comprising an antibody binding domain (AbBD) attached to or modified with a first member of a binding pair to form an adapter-antibody conjugate; (b) providing an antibody conjugate comprising the second antibody or antigen-binding fragment attached to or modified with a second member of the binding pair; and (c) combining the adapter-antibody conjugate and antibody conjugate under conditions where the first and second members of the binding pair bind to each other to form a bispecific antibody.

In another aspect, provided herein are methods of producing a bispecific antibody from a first antibody or antigen-binding fragment and an antibody-adapter fusion comprising a second antibody or antigen-binding fragment fused to an adapter comprising an antibody binding domain (AbBD), the method comprising: site-specifically linking the first antibody or antigen-binding fragment to the antibody-adapter.

Also provided herein are bispecific antibodies produced according to the foregoing methods.

In another aspect, provided herein is a conjugate molecule or an adapter comprising a protein, such as a Protein G HTB1 domain or Protein Z domain, having one or more amino acids or amino acid modifications that are adapted to specifically bind and crosslink to an immunoglobulin. In another aspect, provided herein is a conjugate molecule or an adapter comprising a first antibody binding domain (AbBD) fused to a second antibody binding domains (AbBD), wherein the first AbBD has one or more amino acids or amino acid modifications that are adapted to specifically bind and crosslink to a first immunoglobulin and wherein the second AbBD has one or more amino acids or amino acid modifications that are adapted to specifically bind and crosslink to a second immunoglobulin.

Also provided herein are nucleic acids and vectors that encode the foregoing adapters. Further provided herein are cells that express the foregoing adapters.

In one embodiment, the immunoglobulin is IgG.

In another embodiment, the protein is a recombinant bacterial protein. In another embodiment, the recombinant bacterial protein is Protein Z.

In another embodiment, the recombinant bacterial protein is a subdomain of Protein G.

In another embodiment, the recombinant bacterial protein is a subdomain of Protein A. In another embodiment, the recombinant bacterial protein is a Protein L or a subdomain thereof. In another embodiment, the recombinant bacterial protein is CD4 or a subdomain thereof.

In another embodiment the adapter is an antibody binding domain (AbBD).

In another embodiment, the antibody binding domain crosslinks to the immunoglobulin Fc region. In another embodiment, the antibody binding domain crosslinks to the immunoglobulin Fab region.

The term "Protein Z," as used herein, refers to the Z domain based on B domain of *Staphylococcal aureus* Protein A. The amino acid sequence of wild-type Protein Z is: VDNKFNKEQQNAFYEILHLPNLNEEQRNAFIQSL KDDPSQSANLLAEAKKLNDAQAP KMRM (SEQ ID NO: 1). Photoreactive Protein Z includes those where an amino acid in protein Z has been replaced with benzoylphenylalanine (BPA), such as F13BPA and F5BPA (see underlined amino acids in bold in SEQ ID NO: 1). Examples of other BPA-containing mutants of Protein Z include, for example, but are not limited to, Q32BPA, K35BPA, N28BPA, N23BPA, and L17BPA. Examples of Protein Z variants or mutants include, F5I, such as F5I K35BPA. The amino acid sequence of Protein Z may also include homologous, variant, and fragment sequences having Z domain function. In some embodiments, the amino acid sequence of Protein Z may include an amino acid sequence which is 60, 65, 70, 75, 80, 85, 90, 95, or 99% identity to the sequence set forth in SEQ ID NO: 1.

Figure 6:
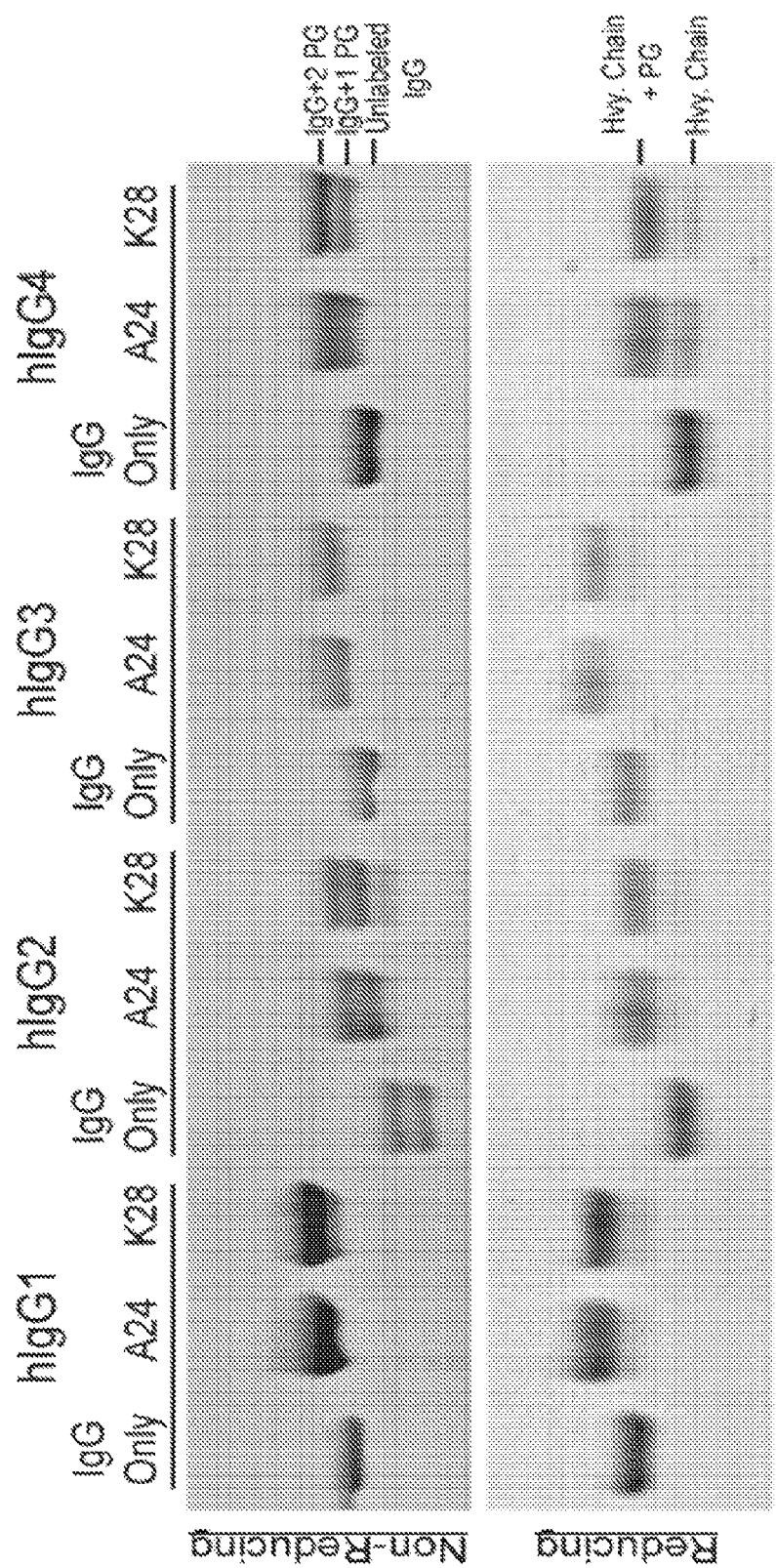
FIG. 6. Non-reducing and reducing SDS-PAGE gels of various human IgG subclasses alone or after photocrosslinking with Protein G-based adapter proteins. The adapter proteins possessed either an A24BPA or K28BPA substitution. Conjugation was done for one hour and 30 minutes using four equivalents of Protein G.

Unless otherwise indicated or the context dictates otherwise, the term "Protein G," as used herein, refers to a B1 domain based of *Streptococcal* Protein G. Preferably, the Protein G is a hypothermophilic variant of a B1 domain based of *Streptococcal* Protein G. The amino acid sequence of Protein G preferably is: MTFKLIINGKTLKGEITIEA VDAAEAEKIFKQYANDYGIDGEWTYDDATKTFTVTE (SEQ ID NO: 2). As described in Example 2, nine Protein G variants were successfully designed and expressed, each having an Fc-facing amino acid substituted by BPA: V21, A24, K28, I29, K31, Q32, D40, E42, W42 (FIG. 12; see underlined amino acids in bold in SEQ ID NO: 2). Two variants, A24BPA and K28BPA, allowed ~100% of all human IgG subtypes to be labeled (FIG. 6). The amino acid sequence of Protein Z may also include homologous, variant, and fragment sequences having B1 domain function. In some embodiments, the amino acid sequence of Protein G may include an amino acid sequence which is 60, 65, 70, 75, 80, 85, 90, 95, or 99% identity to the sequence set forth in SEQ ID NO: 2.

As used herein, the term "Fc domain" encompasses the constant region of an immunoglobulin molecule. The Fc region of an antibody interacts with a number of Fc receptors and ligands, imparting an array of important functional capabilities referred to as effector functions, as described herein. For IgG the Fc region comprises Ig domains CH2 and CH3. An important family of Fc receptors for the IgG isotype are the Fc gamma receptors (FcγRs). These receptors mediate communication between antibodies and the cellular arm of the immune system.

As used herein, the term "Fab domain" encompasses the region of an antibody that binds to antigens. The Fab region is composed of one constant and one variable domain of each of the heavy and the light chains.

As used herein, the term "immunoglobulin G" or "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. As used herein, the term "modified immunoglobulin G" refers to a molecule that is derived from an antibody of the "G" class. As used herein, the term "antibody" refers to a protein consisting of one or more polypeptides substantially encoded by all or part of the recognized immunoglobulin genes. The recognized immunoglobulin genes, for example in humans, include the kappa (κ) lambda (λ) and heavy chain genetic loci, which together comprise the myriad variable region genes, and the constant region genes mu (μ) delta (δ), gamma (γ), sigma (σ) and alpha (α) which encode the IgM, IgD, IgG, IgE, and IgA isotypes or classes, respectively. The term "antibody" is meant to include full-length antibodies, and may refer to a natural antibody from any organism, an engineered antibody, or an antibody generated recombinantly for experimental, therapeutic, or other purposes as further defined below. Furthermore, full-length antibodies comprise conjugates as described and exemplified herein. As used herein, the term "antibody" comprises monoclonal and polyclonal antibodies. Antibodies can be antagonists, agonists, neutralizing, inhibitory, or stimulatory. Specifically included within the definition of "antibody" are full-length antibodies described and exemplified herein. By "full length antibody" herein is meant the structure that constitutes the natural biological form of an antibody, including variable and constant regions.

The "variable region" of an antibody contains the antigen binding determinants of the molecule, and thus determines the specificity of an antibody for its target antigen. The variable region is so named because it is the most distinct in sequence from other antibodies within the same isotype. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

Furthermore, antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

The term "epitope" as used herein refers to a region of the antigen that binds to the antibody or antigen-binding fragment. It is the region of an antigen recognized by a first antibody wherein the binding of the first antibody to the region prevents binding of a second antibody or other bivalent molecule to the region. The region encompasses a particular core sequence or sequences selectively recognized by a class of antibodies. In general, epitopes are comprised by local surface structures that can be formed by contiguous or noncontiguous amino acid sequences.

As used herein, the terms "selectively recognizes", "selectively bind" or "selectively recognized" mean that binding of the antibody, antigen-binding fragment or other bivalent molecule to an epitope is at least 2-fold greater, preferably 2-5 fold greater, and most preferably more than 5-fold greater than the binding of the molecule to an unrelated epitope or than the binding of an antibody, antigen-binding fragment or other bivalent molecule to the epitope, as determined by techniques known in the art and described herein, such as, for example, ELISA or cold displacement assays.

As used herein, the term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes Immunoglobulins include but are not limited to antibodies Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

Depending on the amino acid sequence of the constant domain of their heavy chains, intact antibodies can be assigned to different "classes". There are five-major classes (isotypes) of intact antibodies: IgA, IgD, IgE, IgG, and IgM, and several of these may be further divided into "subclasses", e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known to one skilled in the art.

In one embodiment, the term "antibody" or "antigen-binding fragment" respectively refer to intact molecules as well as functional fragments thereof, such as Fab, a scFv-Fc bivalent molecule, F(ab')$_2$, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

(6) scFv-Fc, is produced in one embodiment, by fusing single-chain Fv (scFv) with a hinge region from an immunoglobulin (Ig) such as an IgG, and Fc regions.

In some embodiments, an antibody provided herein is a monoclonal antibody. In some embodiments, the antigen-binding fragment provided herein is a single chain Fv (scFv), a diabody, a tandem scFv, a scFv-Fc bivalent molecule, an Fab, Fab', Fv, F(ab')$_2$ or an antigen binding scaffold (e.g., affibody, monobody, anticalin, DARPin, Knottin, etc.).

As used herein, the terms "bivalent molecule" or "BY" refer to a molecule capable of binding to two separate targets at the same time. The bivalent molecule is not limited to having two and only two binding domains and can be a polyvalent molecule or a molecule comprised of linked monovalent molecules. The binding domains of the bivalent molecule can selectively recognize the same epitope or different epitopes located on the same target or located on a target that originates from different species. The binding domains can be linked in any of a number of ways including, but not limited to, disulfide bonds, peptide bridging, amide bonds, and other natural or synthetic linkages known in the art (Spatola et al., "Chemistry and Biochemistry of Amino Acids, Peptides and Proteins," B. Weinstein, eds.; Marcel Dekker, New York, p. 267 (1983) (general review); Morley, J. S., "Trends Pharm Sci" (1980) pp. 463-468 (general review); Hudson et al., Int J Pept Prot Res (1979) 14, 177-185; Spatola et al., Life Sci (1986) 38, 1243-1249; Hann, M. M., J Chem Soc Perkin Trans I (1982) 307-314; Almquist et al., J Med Chem (1980) 23, 1392-1398; Jennings-White et al., Tetrahedron Lett (1982) 23, 2533; Szelke et al., European Application EP 45665; Chemical Abstracts 97, 39405 (1982); Holladay, et al., Tetrahedron Lett (1983) 24, 4401-4404; and Hruby, V. J., Life Sci (1982) 31, 189-199).

As used herein, the terms "binds" or "binding" or grammatical equivalents, refer to compositions having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In one embodiment, the antibody or antigen-binding fragment binds its target with a $K_D$ of 0.1 nM-10 mM. In one embodiment, the antibody or antigen-binding fragment binds its target with a $K_D$ of 0.1 nM-1 mM. In one embodiment, the antibody or antigen-binding fragment binds its target with a $K_D$ within the 0.1 nM range. In one embodiment, the antibody or antigen-binding fragment binds its target with a $K_D$ of 0.1-2 nM. In another embodiment, the antibody or antigen-binding fragment binds its target with a $K_D$ of 0.1-1 nM. In another embodiment, the antibody or antigen-binding fragment binds its target with a $K_D$ of 0.05-1 nM. In another embodiment, the antibody or antigen-binding fragment binds its target with a $K_D$ of 0.1-0.5 nM. In another embodiment, the antibody or antigen-binding fragment binds its target with a $K_D$ of 0.1-0.2 nM.

In some embodiments, the antibody or antigen-binding fragment thereof provided herein comprises a modification. In another embodiment, the modification minimizes conformational changes during the shift from displayed to secreted forms of the antibody or antigen-binding fragment. It is to be understood by a skilled artisan that the modification can be a modification known in the art to impart a functional property that would not otherwise be present if it were not for the presence of the modification. Encompassed are antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

In some embodiments, the modification is one as further defined herein below. In some embodiments, the modification is a N-terminus modification. In some embodiments, the modification is a C-terminal modification. In some embodiments, the modification is an N-terminus biotinylation. In some embodiments, the modification is an C-terminus biotinylation. In some embodiments, the secretable form of the antibody or antigen-binding fragment comprises an N-terminal modification that allows binding to an Immunoglobulin (Ig) hinge region. some embodiments, the Ig hinge region is from but is not limited to, an IgA hinge region. In some embodiments, the secretable form of the antibody or antigen-binding fragment comprises an N-terminal modification that allows binding to an enzymatically biotinylatable site. In some embodiments, the secretable form of the antibody or antigen-binding fragment comprises an C-terminal modification that allows binding to an enzymatically biotinylatable site. In some embodiments, biotinylation of said site functionalizes the site to bind to any surface coated with streptavidin, avidin, avidin-derived moieties, or a secondary reagent.

It will be appreciated that the term "modification" can encompass an amino acid modification such as an amino acid substitution, insertion, and/or deletion in a polypeptide sequence.

In one embodiment, a variety of radioactive isotopes are available for the production of radioconjugate antibodies and can be of use in the methods and compositions provided herein. Examples include, but are not limited to, $At^{211}$, $Cu^{64}$, $I^{131}$, $I^{125}$, $Y^{90}$, $Re^{186}$, $Re^{188}$, $Sm^{153}$, $Bi^{212}$, $P^{32}$, and radioactive isotopes of Lu.

In an alternate embodiment, enzymatically active toxin or fragments thereof that can be used in the compositions and methods provided herein include, but are not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

A chemotherapeutic or other cytotoxic agent may be conjugated to the protein, according to the methods provided herein, as an active drug or as a prodrug. The term "prodrug" refers to a precursor or derivative form of a pharmaceutically active substance that is less cytotoxic to tumor cells compared to the parent drug and is capable of being enzymatically activated or converted into the more active parent form. See, for example Wilman, 1986, *Biochemical Society Transactions*, 615th Meeting Belfast, 14:375-382; and Stella et al., "Prodrugs: A Chemical Approach to Targeted Drug Delivery," Directed Drug Delivery, Borchardt et al., (ed.): 247-267, *Humana Press*, 1985. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies and Fc fusions of the compositions and methods as provided herein include but are not limited to any of the aforementioned chemotherapeutic.

In one embodiment, any combination of the protein with the biological active agents specified above, i.e., a cytokine, an enzyme, a chemokine, a radioisotope, an enzymatically active toxin, or a chemotherapeutic agent can be applied.

In one embodiment, a variety of other therapeutic agents may find use for administration with the antibodies and conjugates of the compositions and methods provided herein. In one embodiment, the conjugate comprising an antibody is administered with an anti-angiogenic agent. As used herein, the term "anti-angiogenic agent" refers to a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. In an alternate embodiment, the conjugate is administered with a therapeutic agent that induces or enhances adaptive immune response. In an alternate embodiment, the conjugate is administered with a tyrosine kinase inhibitor. The term "tyrosine kinase inhibitor" refers to a molecule that inhibits to some extent tyrosine kinase activity of a tyrosine kinase as known in the art.

In one embodiment, the conjugates provided herein may be used for various therapeutic purposes. In one embodiment, the conjugates are administered to a subject to treat an antibody-related disorder. In another embodiment, the conjugate proteins are administered to a subject to treat a tumor or a cancer tumor. A "subject" for the purposes of the compositions and methods provided herein includes humans and other animals, preferably mammals and most preferably humans. Thus the conjugates provided herein have both human therapy and veterinary applications. In another embodiment the subject is a mammal, and in yet another embodiment the subject is human. By "condition" or "disease" herein are meant a disorder that may be ameliorated by the administration of a pharmaceutical composition comprising the conjugate of the compositions and methods provided herein. Antibody related disorders include but are not limited to autoimmune diseases, immunological diseases, infectious diseases, inflammatory diseases, neurological diseases, and oncological and neoplastic diseases including cancer.

In another embodiment, provided herein is a nucleic acid construct encoding the conjugate provided herein. In some embodiments, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, provided herein are primers used for amplification and construction of the vectors and nucleic acids provided herein. It is to be understood by a skilled artisan that other primers can be used or designed to arrive at the vectors, nucleic acids and conjugates provided herein.

In one embodiment, provided herein is a vector comprising the nucleic acid encoding for the conjugate components provided herein. In another embodiment, the vector comprises nucleic acid encoding the protein, polypeptides, peptides, antibodies, and recombinant fusions provided herein.

In another embodiment, the nucleic acid can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medusa, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. In another embodiment, a nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which the nucleic acid provided herein has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells (e.g., COS-7, CV1, BHK, CHO, HeLa, LTK, NIH 3T3, 293, PAE, human, human fibroblast, human primary tumor cells, testes cells), insect cells, such as Sf9 (*S. frugipeda*) and *Drosophila*, bacteria, such as *E. coli*, *Streptococcus*, *bacillus*, yeast, such as *S. cerevisiae* (e.g., cdc mutants, cdc25, cell cycle and division mutants, such as ATCC Nos. 42563, 46572, 46573, 44822, 44823, 46590, 46605, 42414, 44824, 42029, 44825, 44826, 42413, 200626, 28199, 200238, 74155, 44827, 74154, 74099, 201204, 48894, 42564, 201487, 48893, 28199, 38598, 201391, 201392), fungal cells, plant cells, embryonic stem cells (e.g., mammalian, such as mouse or human), fibroblasts, muscle cells, neuronal cells, etc. Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

In one embodiment, reporter genes may be incorporated within expression constructs to facilitate identification of transcribed products. Accordingly and in one embodiment of the compositions and methods provided herein, reporter genes utilized are selected from the group consisting of β-galactosidase, chloramphenicol acetyl transferase, luciferase and a fluorescent protein.

In one embodiment, the conjugates are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of conjugates. For example, the bacterial proteins A and G bind to the Fc region. Likewise, the bacterial protein L binds to the Fab region of some antibodies, as of course does the antibody's target antigen. Purification can often be enabled by a particular fusion partner. For example, proteins may be purified using glutathione resin if a GST fusion is employed, $Ni^{+2}$ affinity chromatography if a His-tag is employed, or immobilized anti-flag antibody if a flag-tag is used. The degree of purification necessary will vary depending on the screen or use of the conjugates. In some instances no purification is necessary. For example in one embodiment, if the conjugates are secreted, screening may take place directly from the media. As is well known in the art, some methods of selection do not involve purification of proteins. Thus, for example, if a library of conjugates is made into a phage display library, protein purification may not be performed.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

Described herein are techniques for the rapid production of bispecific antibodies using full-length IgG. These techniques generally do not require any genetic manipulation of the IgG. Any off the shelf IgGs can be used to make the bispecific antibodies.

IgGs are site-specifically modified using photo-reactive antibody binding domains. Antibody binding domains (AbBDs) include Protein A, Protein G, Protein L, CD4 and their subdomains, e.g. B1 domain of Protein G, or engineered subdomains, e.g. Protein Z, HTB1.

In some embodiments, one or more photo reactive groups, e.g. benzophenone, are introduced onto the AbBDs. These can be incorporated into the AbBDs during translation (e.g. benzoylphenylalanine, BPA) using non-natural amino acid incorporation or the AbBDs can be post-modified with a photocrosslinker (e.g. 4-(N-Maleimido)benzophenone). In this case a cysteine would be engineered into the AbBD at the location where the benzophenone is desired. BPA as a photoreactive crosslinker has several favorable properties. Specifically, BPA's benzophenone group can be activated by long wavelength UV light (365 nm), which is not harmful to antibodies or other proteins. Additionally, even after being UV excited to its triplet state, benzophenone can relax back to its unreactive ground state if there are no abstractable hydrogen atoms in close proximity. This allows the photoreactive proteins to be produced and handled in ambient light conditions with low risk of photobleaching. However, other photoreactive crosslinkers can also be used, including those that possess aryl azides, diazirines, or other photoreactive moieties known in the art.

To prepare bispecific antibodies, the AbBDs are fused or modified with a linking module or a member of a binding pair that allows two AbBDs to be linked together.

There are many options for linking modules. A variety of linkers may find use in the compositions and methods provided herein to generate conjugates. The term "linker", "linker sequence", "spacer", "tethering sequence" or grammatical equivalents thereof refer to a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-terminus of proteins or protein domains, linkage via disulfide bonds, and linkage via chemical cross-linking reagents. In one aspect of this embodiment, the linker is a peptide bond, generated by recombinant techniques or peptide synthesis. In another embodiment the linker is a cysteine linker. In yet another embodiment it is a multi-cysteine linker. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. In one embodiment, the linker is from about 1 to 30 amino acids in length. In another embodiment, the linker is from about 1 to 15 amino acids in length. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers, glycine-alanine polymers, alanine-serine polymers, and other flexible linkers such as the tether for the shaker potassium channel, and a large variety of other flexible linkers, as will be appreciated by those in the art. Suitable linkers may also be identified by screening databases of known three-dimensional structures for naturally occurring motifs that can bridge the gap between two polypeptide chains. In one embodiment, the linker is not immunogenic when administered in a human subject. Thus linkers may be chosen such that they have low immunogenicity or are thought to have low immunogenicity. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the compositions and methods provided herein include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). In another embodiment, chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody. The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the components of the conjugates of the compositions and methods provided herein.

In one aspect, the invention provides biological linking modules. These are fused in frame with the AbBDs at the N- or C-terminus.

SpyCatcher and SpyTag.

One AbBD can be fused to SpyCatcher and a second AbBD can be fused to SpyTag. See Zakeri et al., "Peptide tag forming a rapid covalent bond to a protein, through engineering a bacterial adhesin" *PNAS* (2012) vol. 109 no. 12, pgs. E690-E697, doi: 10.1073/pnas.1115485109, which is hereby incorporated by reference in its entirety.

Split Inteins (or Other Intein-Based Systems).

One AbBD can be fused to one half of the split intein and the other AbBD can be fused to the other half.

Heterodimeric proteins that have an affinity for each other (e.g. c-fos and c-jun, leucine zippers, peptide velcro, etc.) can also be used.

Dock-and-Lock.

This system involves two docking proteins, which are fused to the AbBDs. These proteins bring together the two AbBDs. Then a third peptide is used to covalently link the two docking proteins together.

Sortase.

Sortase substrates (e.g. LPXTG and an N-terminal glycine) are fused to the AbBDs and then free or fused sortase is used to ligate the two AbBDs together.

In another aspect, the invention provides chemical linking modules. The AbBDs are modified at their N- or C-terminus with various chemical moieties that can be used to link them together.

Click Chemistries.

One AbBD can be modified with an azide and the other with an alkyne or constrained alkyne (e.g. ADIBO or DBCO). Other popular click chemistries exist (e.g. tetrazine and TCO). Click chemistries can be incorporated using various techniques, e.g. intein-mediated expressed protein ligation, sortase, sortase-tag expressed protein ligation, nonnatural amino acid incorporation, maleimide chemistry, carbodiimide chemistry, NHS chemistry, aldehyde chemistry, chemoenzymatic approaches (e.g. lipoic acid ligase, formylglycine), etc.

In one aspect, the invention provides oligonucleotides. Click chemistries or conventional chemistries are used to attach oligonucleotides (e.g., complementary oligonucleotides) to the AbBDs. The oligonucleotides are then used to bring together (e.g., by hybridization) the two AbBDs.

AbBDs with complementary linking modules (e.g., SpyCatcher and SpyTag) are covalently linked to IgG upon exposure to long UV light (typically long wavelength UV light). The two complementary AbBD-IgG conjugates are then mixed together to form the bispecific antibody.

In other embodiments, a single construct with two photoreactive AbBDs fused together are used to make bispecific antibodies. For example, photo-reactive AbBDs with unique specificity for different IgG isotypes are fused. Therefore, if it is desirable to link together two IgGs with two distinct subclasses, it is not necessary to use a linking module; rather AbBDs that are directly fused together can be used.

Similarly, in other embodiments, IgG homodimers are prepared using AbBDs that are fused together and do not require a linking module.

While certain methods herein are exemplified by making bispecific antibodies, the methods provided here are not limited to making antibody-antibody conjugates. It will be appreciated that the methods provided herein can also be used to make antibody-protein and antibody-enzyme conjugates, as well as other types of antibody-conjugates. In these cases, the second linking module is placed on the protein or enzyme that is to be linked to the AbBD-IgG conjugate, which contains the other half of the linking module, e.g., to make IgG-affibody conjugates.

AbBDs typically bind both heavy chains on IgG. The present methods include techniques to limit AbBD binding to one heavy chain per IgG. Alternatively, IgG with only a single AbBD attached can be isolated.

Pharmaceutical compositions are contemplated wherein fusion conjugate or adopter of the compositions and methods provided herein and one or more therapeutically active agents are formulated. Formulations of the conjugates of the compositions and methods provided herein are prepared for storage by mixing said antibody having the desired degree of purity with optional pharmaceutically acceptable carriers, excipients or stabilizers, in the form of lyophilized formulations or aqueous solutions. Acceptable carriers, excipients, or to stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants or polyethylene glycol (PEG). In another embodiment, the pharmaceutical composition that comprises the conjugate of the compositions and methods provided herein is in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The conjugate molecules disclosed herein may also be formulated as immunoliposomes. A liposome is a small vesicle comprising various types of lipids, phospholipids and/or surfactant that is useful for delivery of a therapeutic agent to a mammal. Liposomes containing the conjugates are prepared by methods known in the art, such as described in Epstein et al., 1985, *PNAS*, 82:3688; Hwang et al., 1980, *PNAS*, 77:4030; U.S. Pat. Nos. 4,485,045; 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, J National Cancer Inst 81:1484).

The conjugate molecules provided herein may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(−)-3-hydroxybutyric acid) which is a microsphere-based delivery system composed of the desired bioactive molecule incorporated into a matrix of poly-DL-lactide-co-glycolide (PLG).

The conjugate molecules may also be linked to the surfaces of nanoparticles using the linking methods provided herein. In one embodiment, the nanoparticles can be used for imaging or therapeutic purposes.

Administration of the pharmaceutical composition comprising the conjugates provided herein, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Example 1: Facile Method for the Site-Specific, Covalent Attachment of Full-Length IgG Bispecific Antibodies:

Bispecific antibodies have emerged as a highly promising treatment for cancer. Bispecific antibodies physically bring T-cells and cancer cells closer together to enhance cancer cell killing. Perhaps best demonstrating the promise of bispecific antibody is blinantumomab, an anti-CD3×anti-CD19 pair, which has produced clinical remission in precursor B cell acute lymphoblastic leukemia (B-ALL) at thousand fold lower dosages than rituximab (anti-CD20 monoclonal antibody) and doing so without needing a secondary T-cell stimulatory signal. Similarly, Catumaxomab, has led to clinical benefit against malignant ascites with just four intraperitoneal infusions totaling 230 μg over 11 days. Conventional antibody therapies require cumulative antibody amounts ranging from 5-20 g per patient and years of therapy. Given these successes, bispecific antibodies can be a paradigm-shifting therapeutic for cancer treatment.

Challenges Associated with Bispecific Antibodies:

Despite the promise of bispecific antibodies, there are many challenges associated with their use, starting with their production. Early methods involved chemically crosslinking two IgGs, which unsurprisingly produced aggregates and very low amounts of functional product. Later, quandroma technology that fused two hydridomas was used. However, due to the random association between the various light and heavy chains, only ~⅛ of the resulting antibodies had the desired dual specificity. Newer technologies have enabled two scFv's to be fused and recombinantly produced. One of the most promising classes of tandem scFv's is termed bispecific T cell engager (BITE), which includes blinantumomab. For agents generated by recombinant engineering (e.g., BiTEs, diabodies, tandem scFvs, dock and lock), limitations include significant amounts of designing and cloning up front to even generate a product, low yields, instability in serum, formation of aggregates or dissociated subunits, reduced functional activity or binding affinity/avidity attributed to steric factors or altered conformations, etc. Agents that lack a constant region also typically exhibit a short in vivo half-life (thus requiring continuous infusion), as well as complete loss of Fc-related effector functions (e.g. ADCC, CDC, and binding to neonatal Fc receptors).

One of the most clinically successful classes of bispecific antibody is Triomab (e.g. Catumaxomab), which is composed of mouse IgG2a and rat IgG2b. Mouse IgG2a and rat IgG2b demonstrate a species-restricted heavy/light chain pairing and result in the production of correct full-length. IgG. Despite the high immunogenicity of this rat/mouse hybrid molecule, it does not constitute a major issue possibly due to the small amounts administered (~100 μg, compared to 3 g for rituximab), the short duration of the treatment (ten days) and the IP route of administration. However, intravenous (IV) injections will be required for other indications. In a phase 1 study for the treatment of non-small cell lung cancer, it was established that the maximum tolerated dose for multiple Triomab IV administration was only 5 μg, together with a pre-medication of dexamethasone and antihistamines. This may limit the broad applicability of Triomab in treating solid tumors.

Adding to the challenges in producing bispecific antibodies is an incomplete understanding of their mode of action. For example, not all anti-CD3 antibodies work equally well to trigger T-cell activation. Given the high cost and time required for production, a methodology that allows bispecific antibodies to be produced from unmodified full-length IgG rapidly and cost-effectively would be highly valuable. We have developed facile methods for the efficient production of bispecific antibodies that will fulfill this need. Since bispecific antibodies may be produced from full-length unmodified IgG, no antibody engineering or cloning is required. Further, bispecific antibodies can be produced with high purity in as little as one day.

Bispecific antibodies can be produced by leveraging two complementary technologies, unnatural amino acid mutagenesis and expressed protein ligation, e.g. sortase-tag expressed protein ligation (STEPL). These techniques are described in greater detail in U.S. Appl. No. 61/799,379 (filed Mar. 15, 2013), in PCT Appl. No. PCT/US2014/030208 entitled "Sortase-Mediated Protein Purification and Ligation" (filed Mar. 17, 2014), in U.S. Appl. No. 61/800, 926 (filed Mar. 15, 2013), and in PCT Appl. No. PCT/US2014/030457 entitled "Method for the Site-Specific Covalent Cross-Linking of Antibodies to Surfaces" (filed Mar. 17, 2014), each of which is hereby incorporated by reference in its entirety. These technologies are combined to recombinantly produce an antibody-binding domain derived from protein Z or protein G with two key features: (1) a photo-crosslinker (benzoylphenylalanine, BPA) within the antibody binding domain and (2) an azide or constrained alkyne moiety (e.g. azadibenzocyclooctyne, ADIBO) at the c-terminus (FIG. 1A). The photocrosslinker allows for covalent linkage to the Fc domain of IgG (FIG. 1B). This prevents protein Z/G from dissociating from the antibody following administration. The azide and constrained alkyne moieties allow the antibody-protein Z/G complexes to be site-specifically and efficiently linked via click chemistry (FIG. 1C). Notably, the formation of homodimers is not possible with this strategy, and the presence of only a single azide or ADIBO moiety on each antibody prevents the formation of aggregates/oligomers.

Sortase-Tag Expressed Protein Ligation (STEPL):

Sortase A (SrtA) is a calcium-assisted transpeptidase that is responsible for anchoring surface proteins to the peptidoglycan cell wall of Gram-positive bacteria. The enzyme cleaves the peptide bond between the amino acids T and G, within the motif, LPXTG. The products remain transiently attached to SrtA, until the N-terminal glycine of another protein displaces the C-terminal fragment and forms a new peptide bond between the two-peptide chains. Recently, we created a single fusion protein construct with LPXTG, SrtA, and a His-tag, respectively, fused to the C-terminal end of Protein Z (FIG. 1A). The Protein Z is released from the affinity column upon ligation to a synthetic peptide with an N-terminal glycine. To produce bispecific antibodies, the peptide is also be labeled with a c-terminal azide or ADIBO. STEPL is site-specific and stoichiometric (i.e 1 azide or ADIBO per protein Z). The purity of the desired conjugate (i.e. Protein Z-azide/ADIBO) is >95% using only a two-fold excess of glycine-azide/ADIBO peptide, per Protein Z (FIG. 2). Therefore, very little excess peptide is required, keeping production cost low. Importantly, this STEPL system links protein purification and conjugation into a single step. Therefore, no post-modification steps are required to label Protein Z with an azide or ADIBO, outside of standard protein purification protocols.

In Vivo Incorporation of Benzoylphenylalanine (BPA) During Protein Expression:

The coding sequence for wild-type Protein Z sequence was cloned into the STEPL-compatible plasmid. To allow for incorporation of the unnatural amino acid, BPA, during translation, site-directed mutagenesis was performed to introduce an amber codon into the IgG binding site of Protein Z (FIG. 1A). Host *E. coli* were co-transformed with the plasmids encoding for photoreactive protein Z or wild-type protein Z and the pEVOL-pBpF plasmid (Addgene), which carries the tRNA/aminoacyl transferase pair. While wild-type Protein Z-STEPL fusion could be expressed in the absence of BPA, the mutant containing the amber codon required BPA for expression. There was no "leaky" background incorporation of other amino acids in response to the amber codon and the expression level for the BPA-containing mutant protein was comparable to that of the wild type Protein Z.

Protein Z-Antibody Crosslinking:

To evaluate the crosslinking capabilities of photoreactive Protein Z, the BPA-protein Z variant was incubated with the humanized IgG1 monoclonal antibody rituximab and exposed to long wavelength UV light (365 nm) for 30 min (FIG. 1B). The extent of crosslinking was assessed via reducing and non-reducing SDS-PAGE gels (FIG. 3). In the reducing gel, one additional band was observed above the heavy chain band, corresponding to Protein Z-crosslinked heavy chain. More than 50% of the heavy chains appear to be crosslinked. On the non-reducing gel, two additional bands are observed in the crosslinked rituximab sample, compared with the non-crosslinked sample. These bands correspond to IgG crosslinked with one or two Protein Zs (FIG. 3B). Image analysis of the non-reducing gels show that 60-80% of rituximab is crosslinked with at least one Protein Z. The binding of a single Protein Z construct eliminates the formation of antibody oligomers, when the azide and ADIBO labeled antibodies are mixed.

Benefits of this Approach:

One of the advantages of this bispecific antibody production method is that any "off-the-shelf," Protein Z-compatible full-length antibody can be used with no need for protein engineering, cloning, or other modifications. Moreover, Protein Z-IgG crosslinking is extremely rapid (~30 min) and efficient. Therefore, this technique is amenable to high-throughput production, which is not currently possible with other techniques. This may allow for rapid screening of bispecific antibody pairs (e.g. different targets, different epitopes, different affinities) for optimal performance. Other advantages include the ability to swap between murine and human antibodies that target the same epitope, genetically modify Protein Z/G to alter immunogenicity, add additional functionality—toxins, imaging agents, drugs, radiopharmaceuticals or other chemical modifications can easily be added to the peptide used for STEPL (or other expressed protein ligation technique)—and there is an opportunity to expand the approach to trimeric, tetrameric, and higher order antibody conjugates by implementing multiple orthogonal click chemistries. Alternatively, IgG can be attached to alternative targeting ligands (e.g. scFv's, affibodies, etc.) or enzymes.

Example 2: Light Activated Site-Specific Conjugation (LASIC) of Native IgGs

Numerous biological applications, from diagnostic assays to immunotherapies, rely on the use of antibody-conjugates. The efficacy of these conjugates can be significantly influenced by the site at which Immunoglobulin G (IgG) is modified. Current methods that provide control over the conjugation site, however, suffer from a number of shortfalls and often require large investments of time and cost. We have developed a novel adapter protein that, when activated by long wavelength UV light, can covalently and site-specifically label the Fc region of nearly any native, full-length IgG, including all human IgG subclasses. Labeling occurs with unprecedented efficiency and speed (>90% after 30 min), with no effect on IgG affinity. The adapter domain can be bacterially expressed and customized to contain a variety of moieties (e.g., biotin, azide fluorophores), making reliable and efficient conjugation of antibodies widely accessible.

Monoclonal antibodies, because of their broad repertoire of targets and exquisite selectivity, have become an essential component for a wide range of biological applications, from diagnostic assays to immunotherapies. Many of these applications require Immunoglobulin G (IgG) to be modified with a chemical (e.g. biotin, contrast agent, drug, nanoparticle) or biological agent (e.g. enzyme, second antibody).

While these diverse antibody formats are commonplace, their complex structures still pose various developmental and production challenges. A salient hurdle involves how to attach the functional moiety at specific locations away from the binding pocket of the antigen binding Fab domain, so as to preserve binding affinity and obtain homogenous products. Site-specific modifications have been widely shown to improve the performance and efficacy of antibody-conjugates in almost every known application.

Several enzymatic and recombinant based approaches have been utilized to enable the site-specific modification of IgG; however, these methods are lengthy and expensive, and often require cloning and cell line development for each construct. Despite the exploding interest in site-specifically modified antibody conjugates, these barriers limit their production to specially equipped labs and severely constrain the number and types of conjugates that can be made. This not only prevents the use of optimal antibody constructs for common laboratory assays, but also stunts the discovery and exploration of new antibody-based therapeutics, and hampers our understanding into the mechanisms of actions of these new formats.

A better approach for developing antibody conjugates would take advantage of the large library of existing antibodies. A means to conjugate existing native antibodies site-specially, rapidly and inexpensively can become an enabling technology to further antibody conjugate discovery and design. We have developed such as a platform, termed LASIC (Light Activated SIte-specific Conjugation) that enables highly efficient and versatile conjugation of nearly all IgGs, including all human subtypes.

Figure 5:
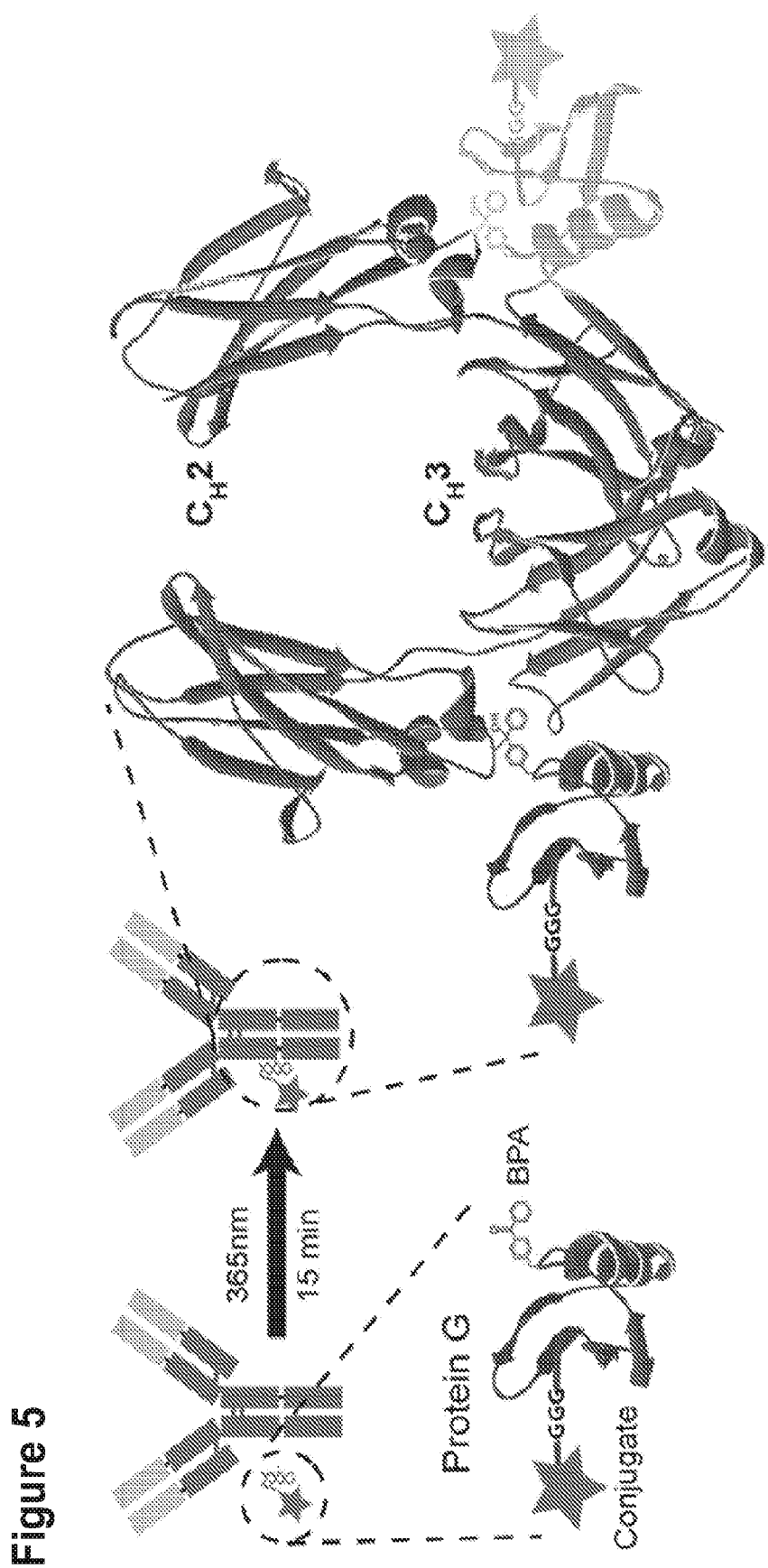
FIG. 5. Illustration of IgG being photocrosslinked with a Protein G-based adapter protein. The Protein G adapter (blue) contains a customizable conjugate at its C-terminus and the unnatural amino acid benzoylphenylalanine (BPA), whose UV-active benzophenone side chain is shown in red, in the Fc binding domain. When bound to the Fc region of IgG and activated by long wavelength UV light (365 nm), a covalent bond is formed between Protein G and IgG. Either one or two Protein Gs can be conjugated onto each Fc (second one is shown faded).

LASIC uses a small adapter protein that is engineered to contain the photoreactive non-natural amino acid benzoyl-phenylalanine (BPA) in its IgG binding domain, as well as a customizable reactive moiety at its C-terminus (FIG. 5). While we previously developed an adapter protein based on Protein A, it showed moderate to no conjugation towards human IgG subtypes. We therefore reasoned that the more broadly binding Protein G might serve as a better platform for LASIC. Protein G is derived from *Streptococcal* bacteria and can naturally bind to a broad range of IgGs at the CH2-CH3 junction. However, the non-covalent nature of the association between Protein G and IgG makes it ill-suited for making antibody conjugates. Although covalently linking Protein G onto IgG has been done using both chemical and photo-activated means, these methods were plagued either by decreased IgG affinity or by complex production and poor efficiency.

LASIC adapters, which possess a BPA crosslinker only in the Fc-binding domain, gives homogeneous products by forming only one covalent bond with IgG, rather than randomly labeling lysines as is the case with chemical crosslinking (FIG. 5). In addition, by recombinantly producing LASIC adapters using a well-established *E Coli*. expression system that can incorporate BPA into proteins via an amber-tRNA suppressor aminoacyl-synthase pair, adapters with BPA in different locations can be efficiently produced and tested against different antibodies.

Figure 12:
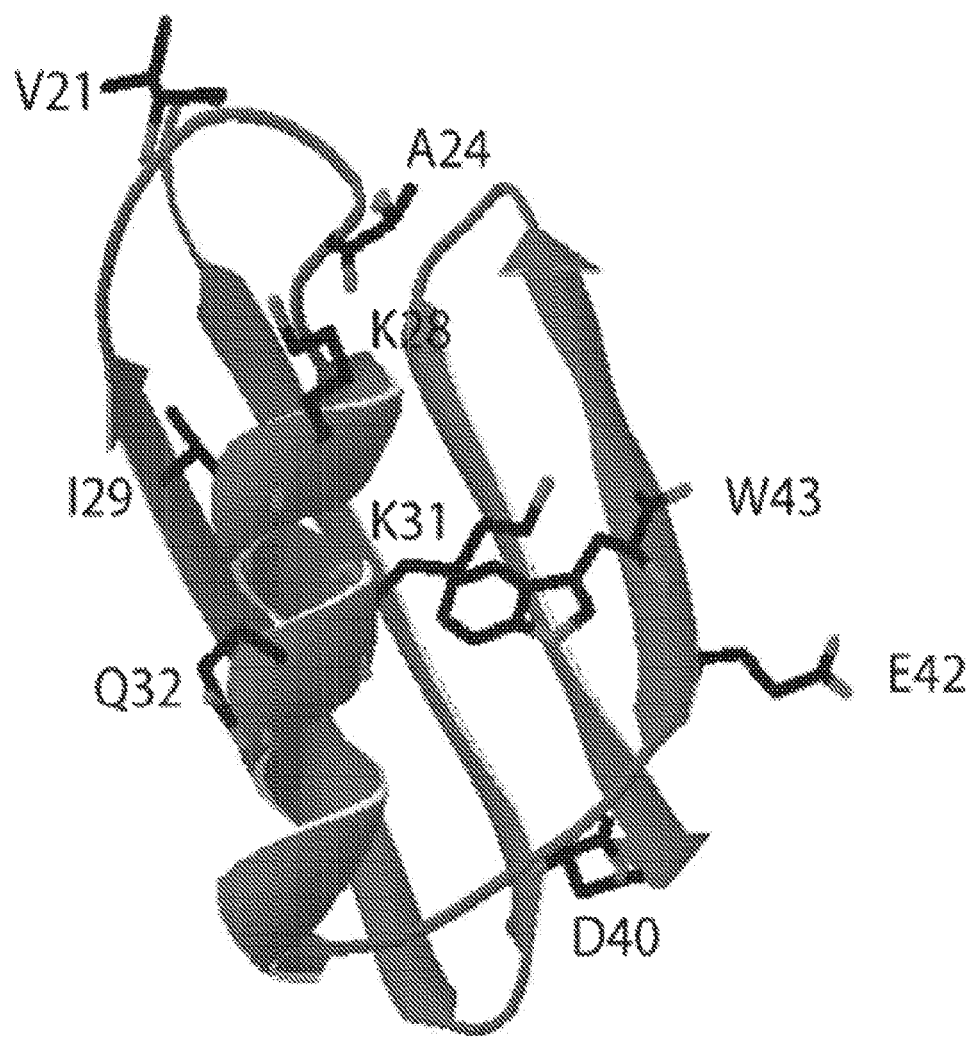
FIG. 12. Protein G with selected side chains depicted.
Figure 13A:
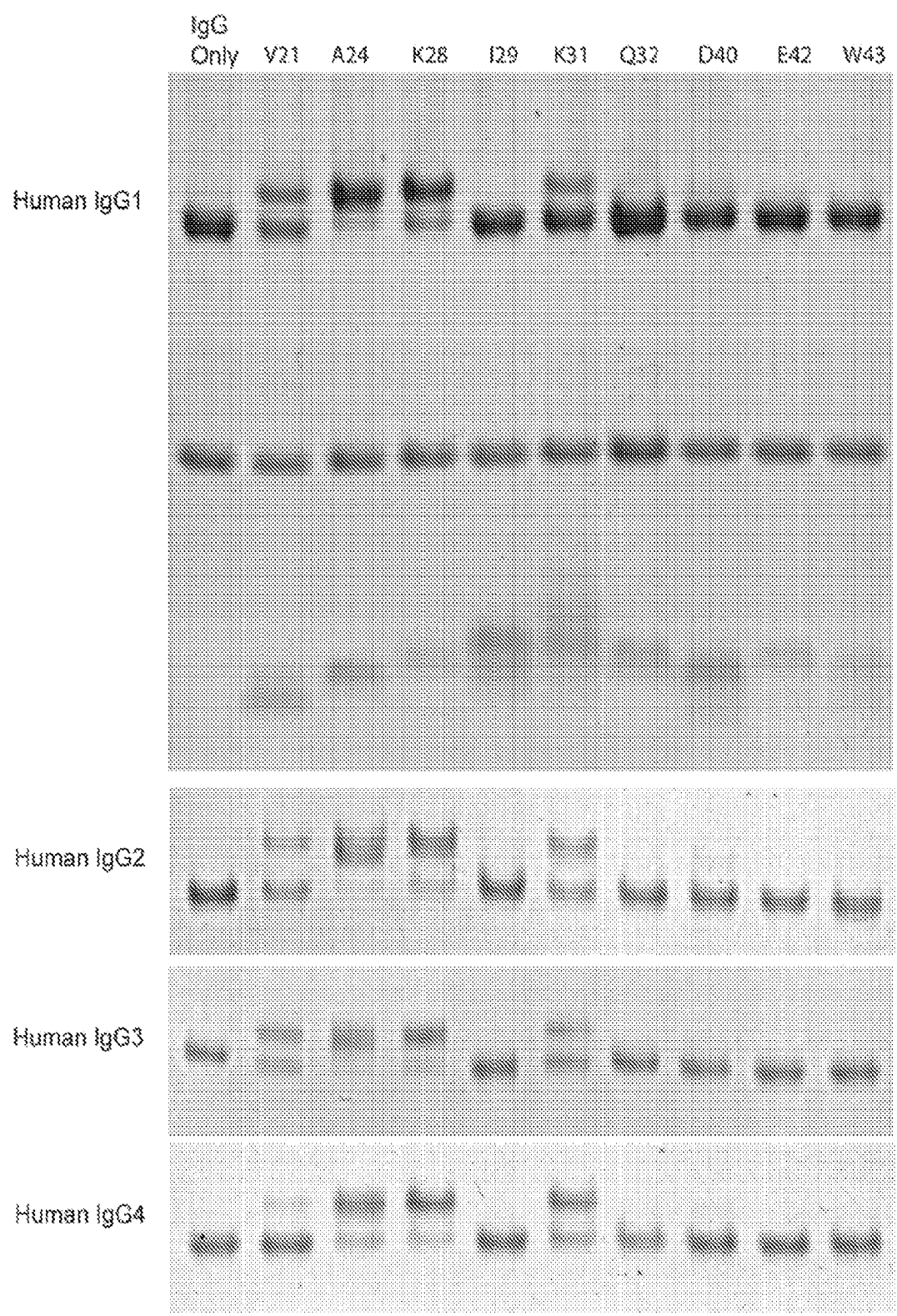
FIG. 13. Screening Protein G adapters for ability to label (A) human and (B) mice IgGs. Reducing SDS-PAGE gel showing that human IgG1 (cetuximab) can be specifically conjugated on the heavy chain by several different Protein G adapters. A24Bpa and K28Bpa showed the best conjugation efficiencies.
Figure 13B:
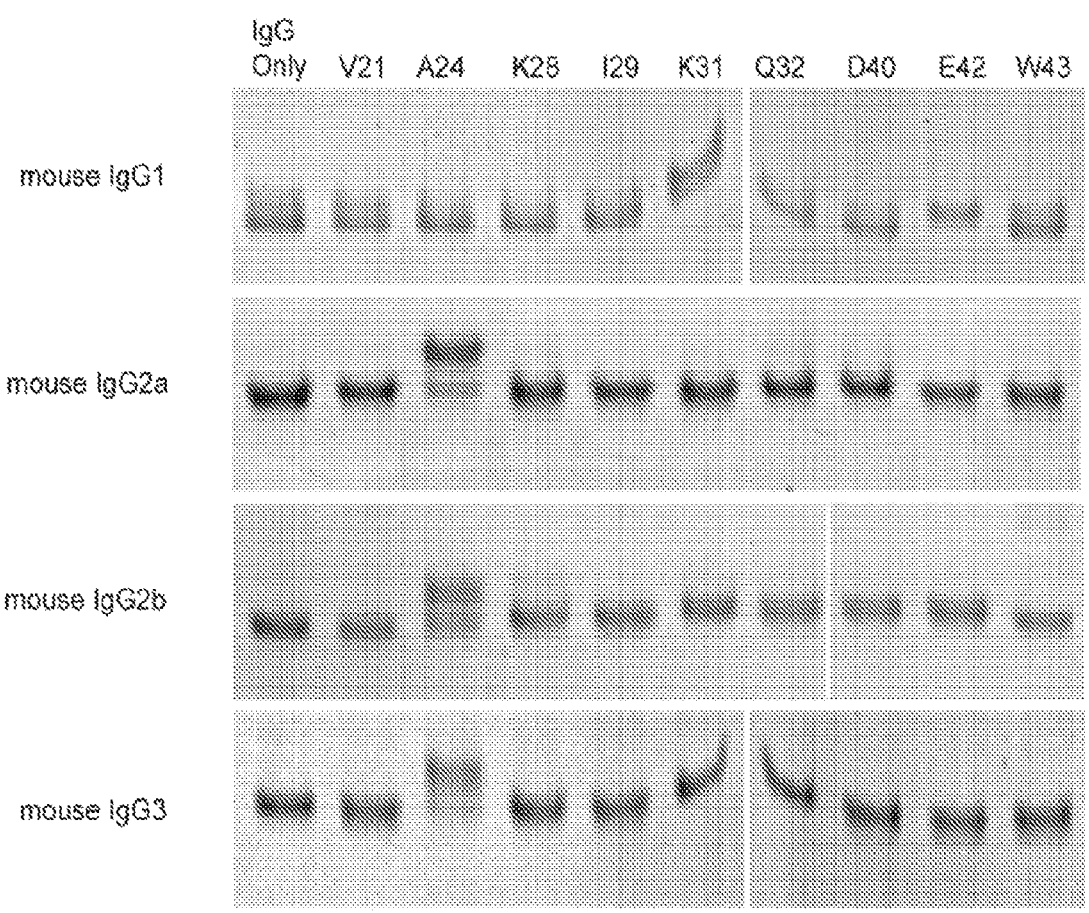

To minimize the "footprint" of the LASIC adapter and to ensure Fc-specific conjugation, we chose to use a small (6.5 kD), thermally stable domain of Protein G (HTB1), with a mutation to disable Fab-binding, as the parental molecule. We successfully designed and expressed nine Protein G variants, each having an Fc-facing amino acid substituted by BPA: V21, A24, K28, I29, K31, Q32, D40, E42, W42 (FIG. 12). The yields of expression for all variants were high at around 5 mg/mL, consistent with previous reports of BPA incorporation into proteins. Next, we screened these variants for their ability to covalently label a range of IgG isotypes from various hosts, upon exposure to long wavelength UV light (FIG. 13A-C). Since each IgG is composed of two identical heavy chains, it can be labeled with up to two Protein G-based adapters, which can be deciphered using non-reducing SDS-PAGE. We found two variants, A24BPA and K28BPA, that allowed ~100% of all human IgG subclasses to be labeled with at least one adapter protein (FIG. 6). More than 90% of all human IgG subtypes were labeled with two adapter proteins (i.e. one adapter protein per heavy chain). In addition, A24BPA is also capable of conjugating most mice (mIgG 2a, 2b, 2c, 3) as well as some rat and rabbit subtypes (rat 2c, rabbit polyclonal) with similar efficiencies (FIG. 14B, C). It has been known that BPA preferentially crosslinks methionine residues. Indeed, a three-dimensional model of the IgG-Protein G complex shows that A24 and K28 come in very close proximity to Met252 and Met482 on IgG, respectively (FIG. 14A). In fact Met252 is found on all IgG that are efficiently labeled with A24BPA, while the same applies for Met428 and K28BPA (FIG. 14B).

Figure 7A:
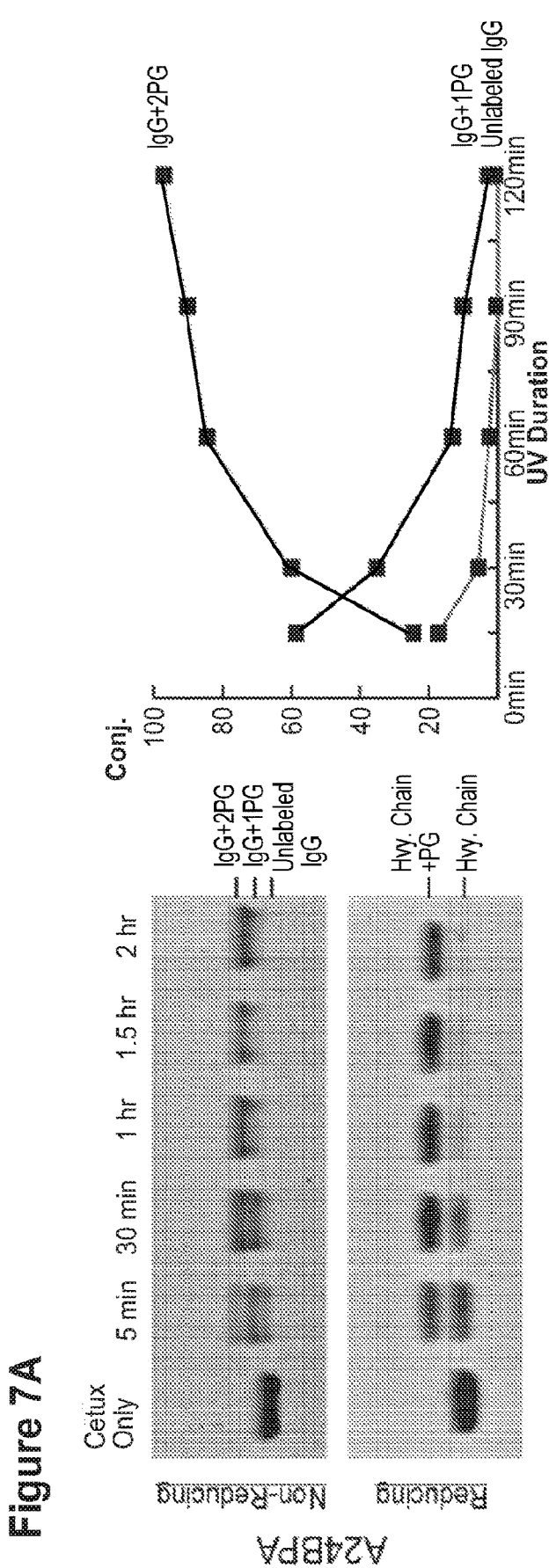
FIG. 7. Kinetics and efficiency of IgG-adapter protein crosslinking. Non-reducing and reducing SDS-PAGE of cetuximab (Cetux, human IgG1) alone or after photocrosslinking with Protein G (PG)-based adapter proteins. The adapter proteins possessed either an (A) A24BPA or (B) K28BPA substitution. UV crosslinking was performed for varying periods of time using four equivalents of the adapter proteins. Image analysis of non-reducing gels are shown on the right. (C) UV crosslinking was performed for one hour and 30 minutes with various molar ratios of adapter protein-to-IgG. The adapter proteins possessed either an A24BPA or K28BPA substitution. Non-reducing and reducing SDS-PAGE gels of cetuximab alone or after photocrosslinking with the Protein G-based adapter proteins are shown. Image analysis of non-reducing gels are shown on the right.
Figure 7B:
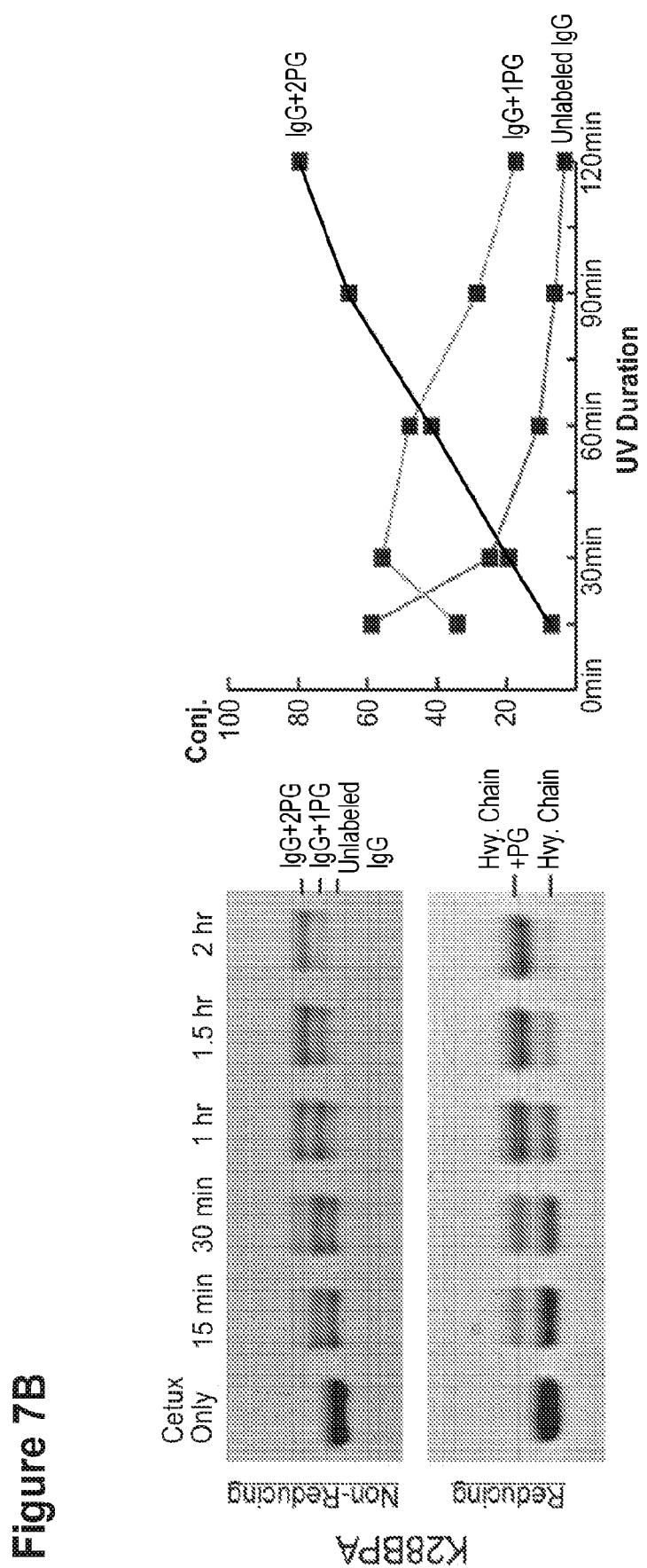

LASIC using A24BPA and K28BPA demonstrated unprecedented fast kinetics. After only 15 minutes of light exposure, more than 80% of IgG were conjugated by one or two A24BPA adapters, while the level reached 95% by 30 minutes (FIG. 7A). K28BPA reacted quickly as well, reaching 75% and 90% conjugation after 30 minutes and 1 hour respectively. The reaction was nearly stoichiometric with complete conjugation of IgG using only one equivalent of A24BPA (FIG. 7B). The fast conjugation kinetics by LASIC adapters is a significant improvement over the performance reported previously using with photoactive protein A or Protein G, where only around 50% of human IgG1 and IgG4 were conjugated after one hour, and negligible or no conjugation was seen for human IgG2 and IgG3, respectively. Similar conjugation efficiencies are reproducible for different IgGs of the same isotype. Similar results are also achievable using other readily available UV light sources and in a variety of common buffers (data not shown).

Figure 8:
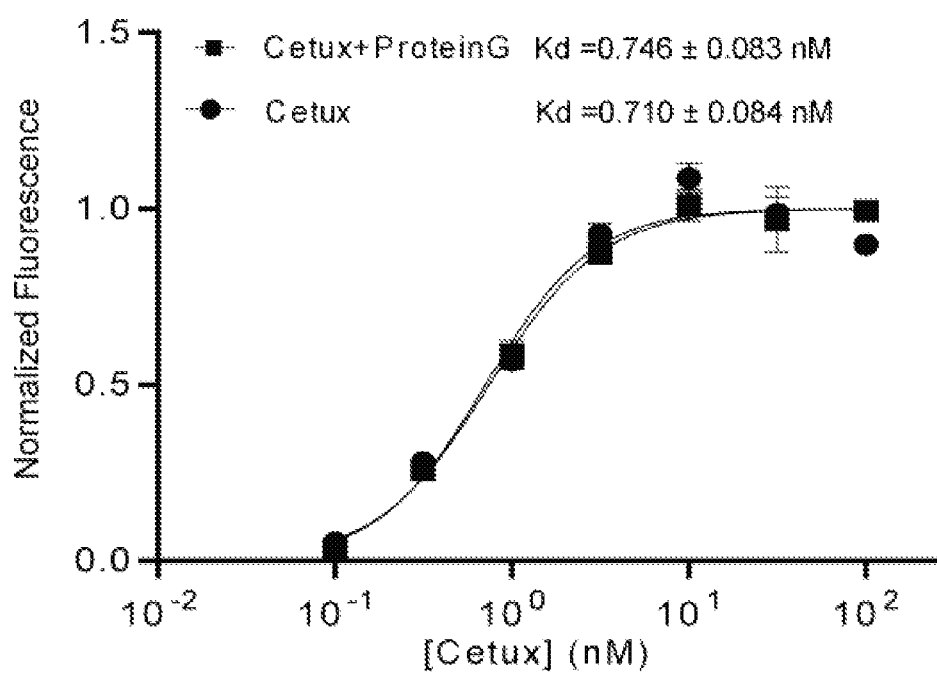
FIG. 8. Antibody binding affinity with and without LASIC. Unmodified Cetuximab (Human IgG1 anti-human EGFR antibodies), or Cetuximab that was subject to LASIC using the A24BPA Protein G adapter protein, were applied to EGFR positive KB cells. The extent of cell labeling was quantified by flow cytometry using a fluorescent anti-human secondary antibody.
Figure 9:
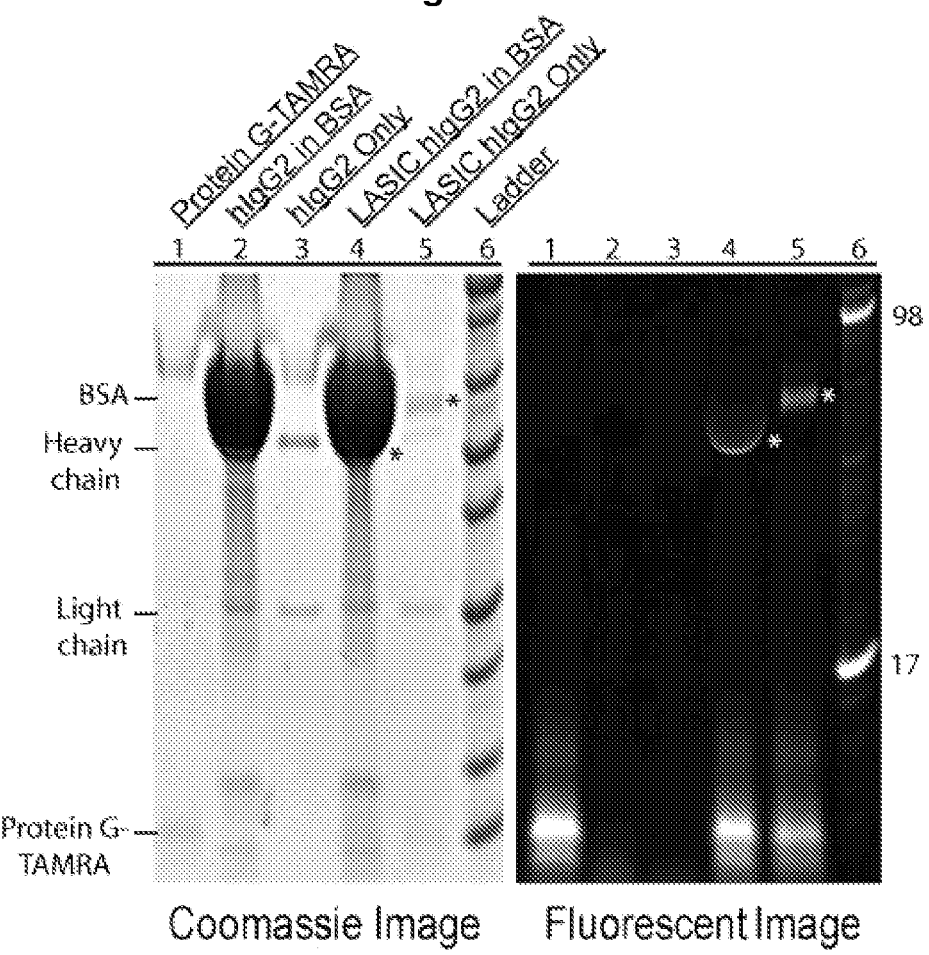
FIG. 9. Effect of impure IgG samples on LASIC. 0.25 μg of Human IgG2, either alone (lanes 3, 5) or with 25 μg BSA (lanes 2, 4), were conjugated with a TAMRA labeled Protein G adapter protein (lane 1). Samples were run on an SDS-PAGE reducing gel and white light and fluorescence images of the gel were acquired.
Figure 15:
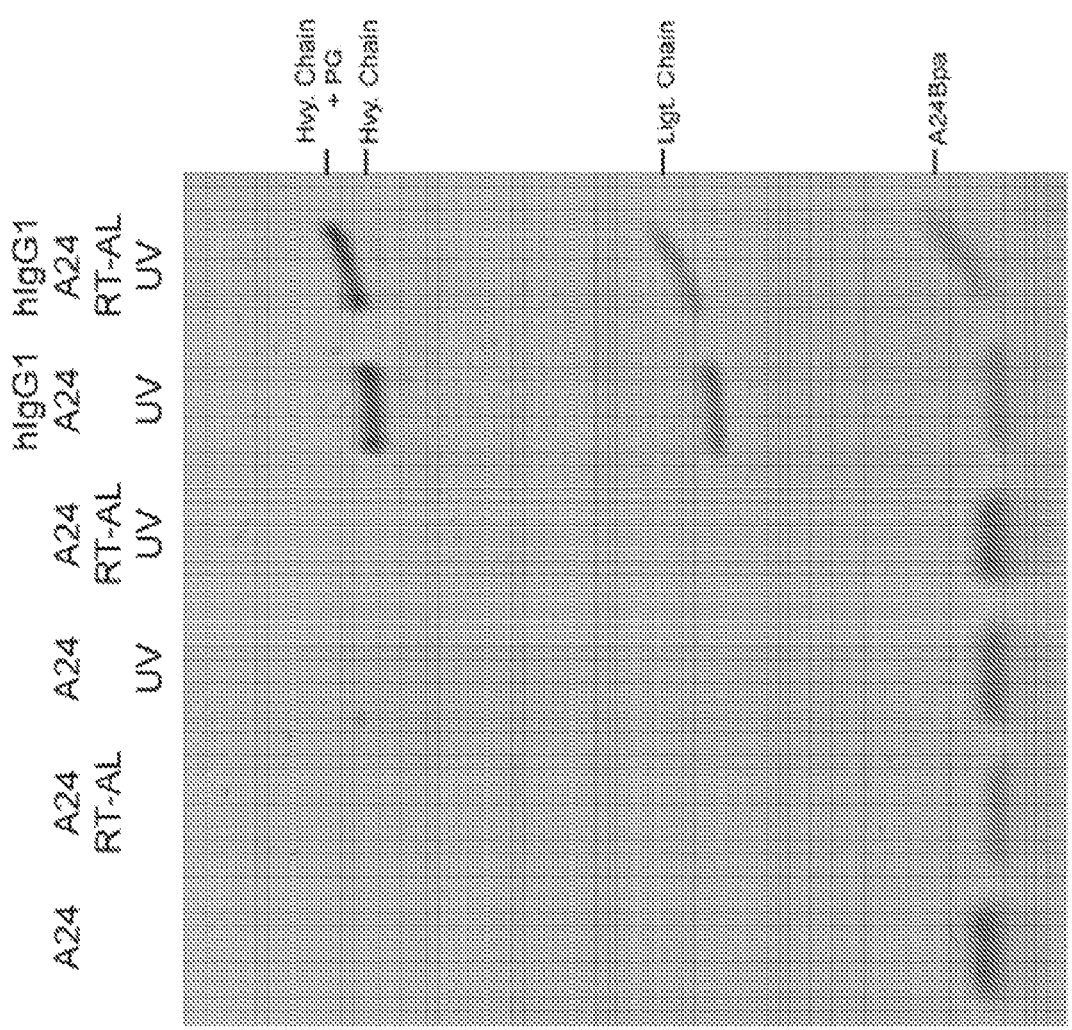
FIG. 15. Storage of Protein G in room temperature (RT) and under ambient lighting (AL) does not affect its ability to label IgG.

The structural stability of the Protein G HTB1 domain gives LASIC adapters a long shelf life even at room temperature, with no detectable loss of activity even after weeks of storage (FIG. 15). The use of BPA, which is only activated by non-harmful long wavelength UV light (365 nm) and is only quenched if in close proximity to a target (10 Å) with which it can form a covalent bond, makes the LASIC adapter safe to use, stable under ambient light, and non-reactive towards other proteins that it cannot bind (FIG. 15). To demonstrate the preservation of antigen binding after LASIC, we first conjugated the human IgG1 anti-human EGFR antibody (cetuximab) with the A24BPA adapter. Next we applied either unmodified cetuximab or LASIC treated cetuximab to EGFR-positive KB cells followed by detection using a fluorescent anti-human secondary antibody. Analysis of the fluorescent signals by a plate-reader indicated that both the unmodified and LASIC treated cetuximab showed similar binding affinity to the target cell line, demonstrating the gentle nature of photo-conjugation (FIG. 8). LASIC's exquisite specificity towards IgG allows conjugation to be done even in the presence of other proteins. This was shown by labeling hIgG2, either by itself or in 1% BSA solution, with a TAMRA (5-Carboxytetramethylrhodamine) dye-tagged LASIC adapter, followed by analysis using reducing SDS-PAGE gel (FIG. 9). While similarly high level of IgG2 heavy chains were labeled by the Protein G with or without BSA, as determined from the fluorescent image, none of the BSA was labeled despite being present at more than 200 times molar excess.

Figure 10:
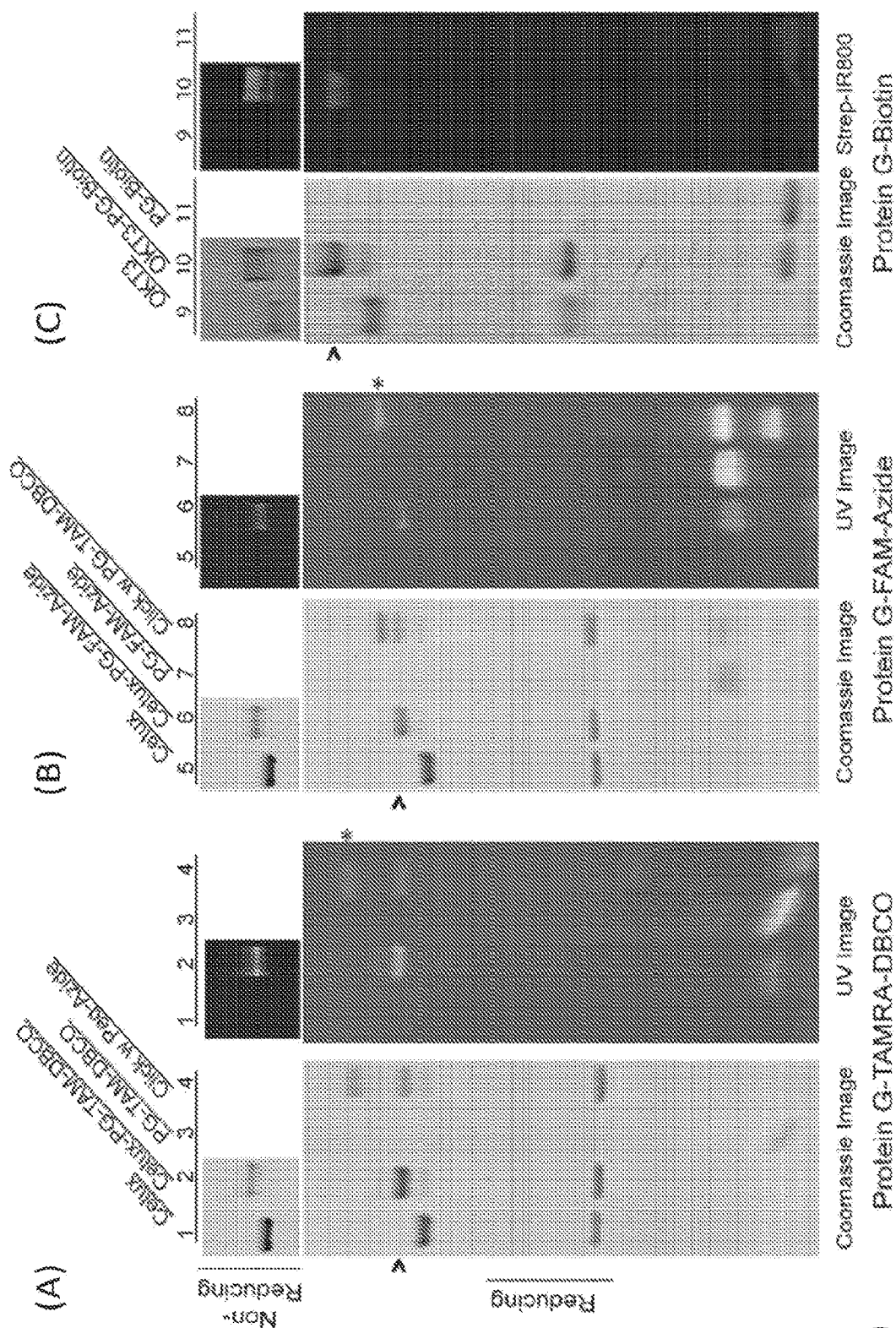
FIG. 10. Modification of IgG with various functional moieties using Protein G adapters. Protein G adapters made with peptides containing either A) TAMRA-DBCO (lane 3), B) FAM-Azide (lane 7), or C) Biotin (lane 11), were LASIC conjugated onto human IgG1 (Cetux, lanes 2 and 6) or mouse IgG2a (OKT3, lane 10). Unconjugated IgGs are shown in lanes 1 (Cetux), 5 (Cetux), and 9 (OKT3). Conjugates remained active as demonstrated by click reactions (Lane 4: Click with Peg-Azide; Lane 8: Click with PG-TAMRA-DBCO) or by Western blot with Streptavind-IRdye800 (lane 10). The arrow (>) indicates Protein G-labeled to heavy chains; The asterisk (*) indicates click product).

In order to produce LASIC adapters with a variety of C-terminal modifications we used the sortase expressed protein ligation (STEPL) technology, developed in our lab, to incorporate various moieties during the recombinant protein purification process. To demonstrate the versatility of this approach, we introduced three different Gly-Gly-Gly N-terminated peptides containing either a biotin, a 5-TAMRA dye along with a dibenzocyclooctyl (DBCO), or a 5-FAM (5-Carboxyfluorescein) dye along with an azide. The resulting adapters were then photo-conjugated to IgG (FIG. 10). As assayed by SDS-PAGE, nearly all of the heavy chains of IgGs were conferred with the functionalities carried by their respective Protein G adapters. There was no decrease in the conjugation efficiency as the moieties are on the C-terminus of the LASIC adapter and hence do not interfere with IgG binding. Since N-terminal triglycine peptides can be quickly and inexpensively synthesized, other reactive groups can be efficiently conjugated onto IgGs just as easily using LASIC.

Figure 11:
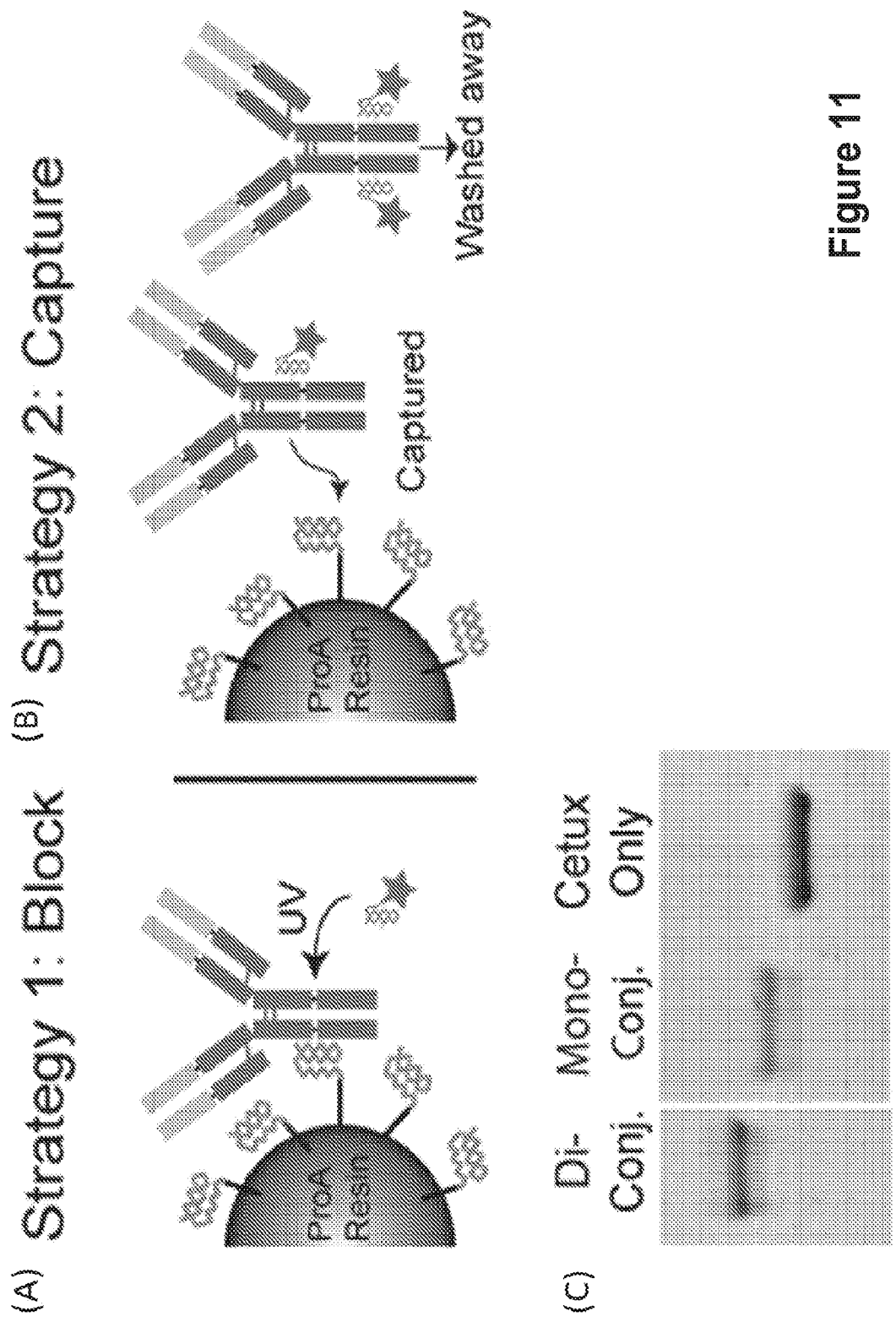
FIG. 11. Controlled labeling of IgG with one or two Protein G adapters. (A) Schematic of IgG being labelled with a single Protein G adapter (i.e. mono-conjugated product) by first preadsorbing IgG onto Protein A or G resins, leaving only one heavy chain available for conjugation. (B) Schematic describing the purification of mono-conjugated product by capturing it from product mixtures of mono- and di-conjugated products. Di-conjugated IgGs cannot bind to Protein A or G resin. (C) Non-reducing SDS-PAGE gel showing mono-conjugated Cetuximab using the method described in (B).

One feature of using a Protein G-based adapter is that both IgG heavy chains can be modified. While this may be preferred when maximum conjugation is important, in some instances it may be desirable to introduce only a single modification onto IgG. With LASIC it is possible to obtain mono-conjugated IgGs by slightly altering the conjugation or purification protocol (FIG. 11). Since the Fc site bound by LASIC adapters overlaps with the natural binding site of wild-type Protein G and Protein A, pre-adsorbing the IgG onto either Protein A or Protein G resin effectively blocks one of the two heavy chains, therefore giving only one conjugate per IgG after LASIC treatment. A similar approach involves absorbing IgG onto resins containing the photo-reactive antibody binding domains. Then after photocrosslinking the adapter-IgG conjugates can be released from the resin using various methods known in the art, including the STEPL approach. Alternatively, as di-conjugated products cannot bind Protein A or Protein G, mono-conjugated product can also be captured from a mixture of di- and mono-conjugated IgGs using Protein A or Protein G resin. The ability to control the number of conjugates on the IgG affords an additional level of control, by allowing, for example, one to tailor the drug to antibody ratio when making antibody-drug conjugates (ADCs). Additionally, the ability of mono-conjugated product to bind to Protein A and G columns also greatly eases the purification of these conjugates. Furthermore, mono-conjugated IgG leaves one Fc-receptor binding site available for natural effector functions, including antibody dependent cell-mediated cytotoxicity (ADCC) and FcRn-mediated IgG recycling.

In summary, we have demonstrated that by using a recombinant Protein G-based adapter, one can efficiently photo-conjugate IgGs with a variety of moieties. Given the tremendous potential of site-specific antibody conjugates, there is a need for generating them more efficiently, ideally from full length IgGs so as to take advantage of their existing vast library, validated binding properties and ready accessibility. Thus, the ability to site-specially conjugate nearly any off-the-shelf IgG is an enabling technology that opens up a variety of applications and may allow the development of antibody conjugates to be "crowd-sourced" by researchers at large.

Example 3: Formation of Bispecific Antibodies

To prepare bispecific antibodies, photoreactive antibody binding domains, e.g. Protein Z or Protein G adapters, can be modified with a linking module or a member of a binding pair that allows two antibody binding domains (i.e. adapters) to be linked together. There are many options for linking modules and they can generally be broken into three categories: biological linking modules, chemical linking modules, or oligonucleotides.

Biological linking modules can be fused in frame with the photoreactive AbBDs at the N- or C-terminus. Examples, of biological linking modules include SpyCatcher/SpyTag, split inteins, heterodimeric proteins that possess an affinity for each other (e.g., c-fos and c-jun, leucine zippers, peptide velcro, etc.), dock-and-lock proteins, sortase substrates, etc.

Figure 16:
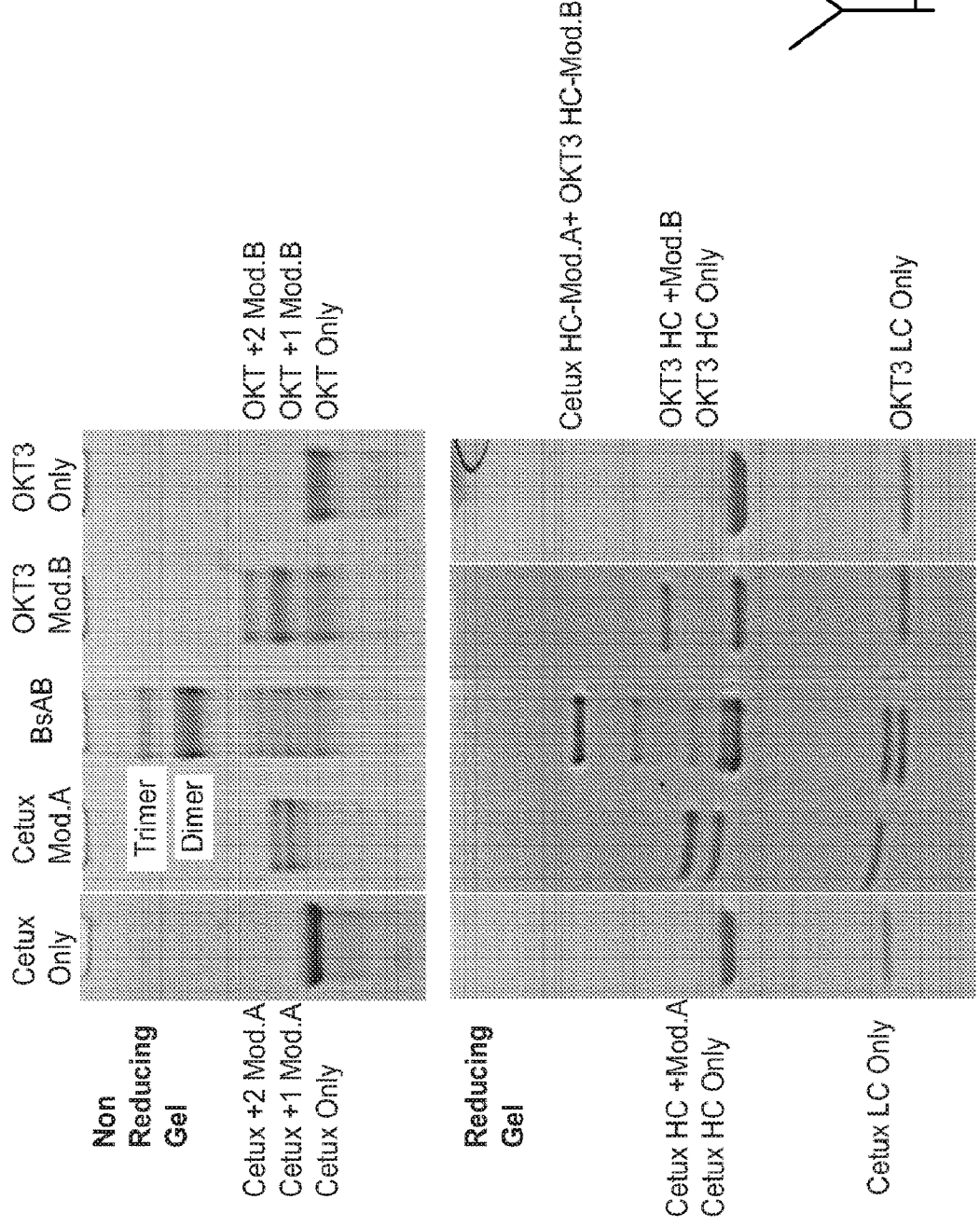
FIG. 16. Native IgGs (cetuximab and OKT3) were site-specifically modified on their heavy chains using either SpyTag (Mod.A) or SpyCatcher (Mod.B). SpyCatcher reacts specifically with SpyTag, to give bispecific IgG dimers that are entirely composed of two different IgG (cetuximab× OKT3).
Figure 17:
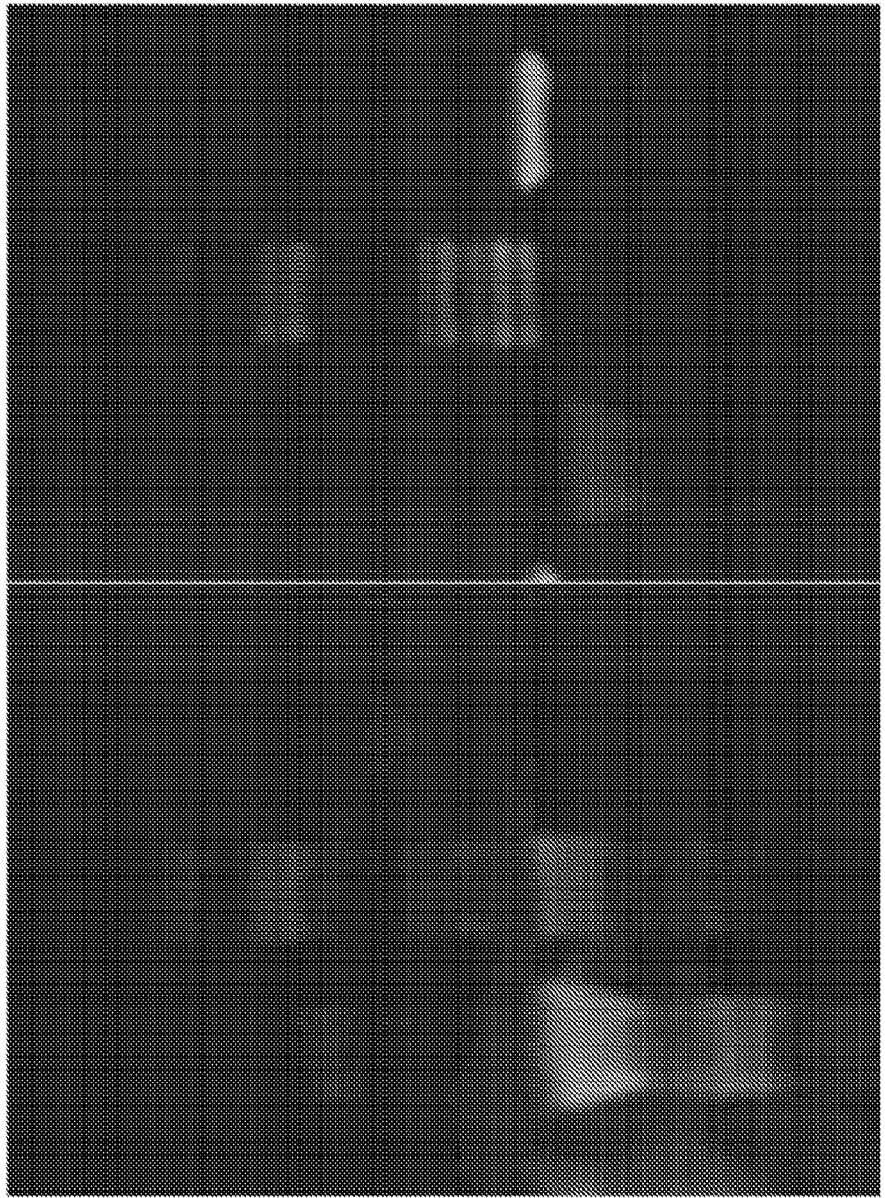
FIG. 17. Bispecificity Confirmed by Western. Western blotting confirms heterodimer formation. A non-reducing SDS-PAGE was probed first with anti-mouse IRdye800 2' (labeling OKT3). The blot was then stripped, followed by anti-human IRdey800 2' (labeling Cetux).

To demonstrate proof-of-principle, SpyTag (Mod.A) and SpyCatcher (Mod.B) were fused in frame at the C-terminal end of the Protein G adapters (FIG. 16). Note that with this approach, expressed protein ligation (e.g. STEPL) is not required to form bispecific antibodies, but could still be used to add additional functionality at the C-terminus of the Protein G adapter-SpyCatcher/SpyTag fusion protein (e.g. imaging agent, drug, etc.). Once the SpyTag and SpyCatcher fusion proteins were expressed and purified, they were photocrosslinked to cetuximab and OKT3 antibodies, respectively (FIG. 16, lanes 2 and 4). The unlabeled antibodies are shown in lanes 1 and 5, for comparison. Covalent linkage of the adapter protein resulted in a clear upward shift of the IgG band in the non-reducing gel and the heavy chain band in the reducing gel. The non-reducing gel confirmed that nearly all of the IgG was labeled with one or two adapters. Mixing of the two adapter-IgG conjugates resulted in the specific formation of bispecific antibodies (FIG. 16, lane 3; dimer). Some antibody monomers still exist as well as some higher order conjugates (e.g. trimers), but the predominant species are bispecific antibodies. Since, SpyCatcher forms a covalent linkage exclusively with SpyTag and not itself, and vice versa, the bispecific antibody that is formed is a heterodimer consisting of one cetuximab antibody and one OKT3 antibody. This was confirmed via western blotting (FIG. 17). Specifically, OKT3, cetuximab, and the bispecific antibody were run on non-reducing SDS-polyacrylamide gel. The OKT3 was probed using a anti-mouse secondary antibody labeled with IRdye800. The blot was then stripped, and subsequently labeled with an anti-human secondary antibody labeled with IRdey800. The OKT3 was only labeled with the anti-mouse secondary antibody. The cetuximab was only labeled with the anti-human secondary antibody. The bispecific antibody was labeled with both secondary antibodies.

Figure 18:
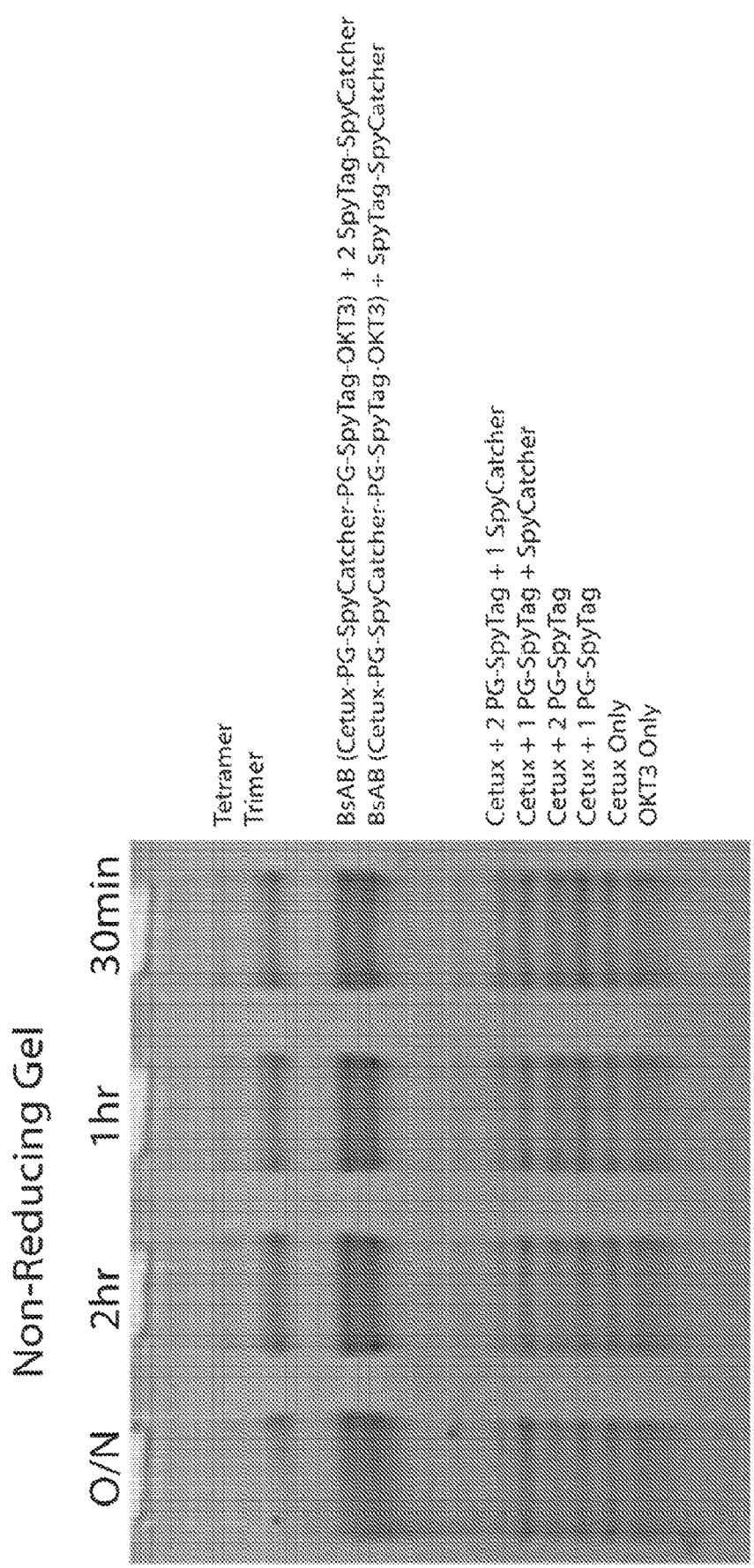
FIG. 18. Kinetics of bispecific antibody formation. Dimer formation is efficient and stoichiometric. Yield is >50%, of total inputting IgGs. It is reproducible at 0.5-1 mg scale. Modification of individual IgG with either Mod.A (SpyTag) or Mod.B (SpyCatcher) takes 60-120 min. Bispecific antibody formation is fast. Nearly plateaus after 30 minutes. No increase in multimer formation seen over time, which is likely due to unfavorable sterics effects.

Bispecific antibody formation using SpyCatcher and SpyTag linking modules is efficient and stoichiometric (FIG. 18). Yield is >50%, of total inputting IgGs. It is also reproducible. Covalent modification of individual IgG with either SpyCatcher- or SpyTag-adapter proteins takes less than 120 min Bispecific antibody formation is fast, nearly plateauing after 30 minutes. No increase in multimer formation is seen over time, which is likely due to unfavorable sterics effects.

Highly pure bispecific antibody samples can be obtained by performing FPLC (FIG. 19) or other standard purification methods. Alternatively, highly pure samples can be obtained if IgG is only modified with an adapter protein on one of its heavy chains, since this prevents the formation of trimer and other higher order species.

As an alternative to biological linking modules, chemical linking modules can also be added to the photoreactive AbBDs at or near the N- or C-terminus. Examples, of chemical linking modules include azide/alkyne, azide/DBCO, tetrazine/TCO, aldehyde/oxyamine, etc. Click chemistry pairs are a favorable choice since they are bio-orthoganol and highly efficient, but other chemical linking modules known in the art can just as easily be used.

Figure 20:
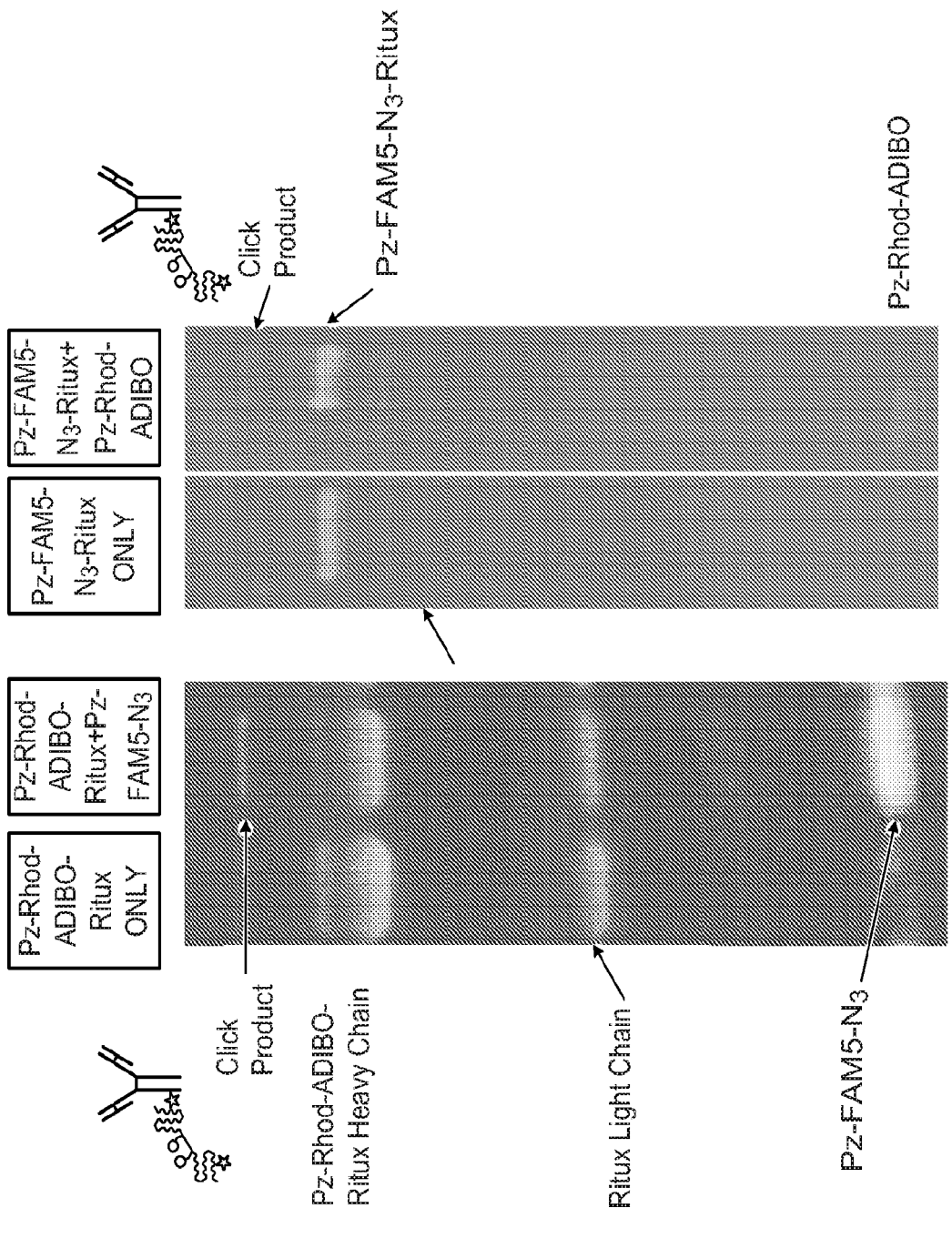
FIG. 20. Modular bispecific antibodies made using azide-DBCO click chemistry. Protein Z-IgG was reacted with second Protein Z (i.e. representative second "targeting to ligand").

To demonstrate proof-of-principle, dibenzocyclooctyne (referred to as DBCO or ADIBO) and azide ($N_3$) labeled peptides were ligated to the C-terminal end of the Protein Z adapters via STEPL (FIG. 20). The ADIBO- and azide-labeled adapters were then both photocrosslinked to rituximab antibodies (FIG. 20, lanes 1 and 3). The ADIBO-IgG conjugate gives a red fluorescence signal on the gel since a TAMRA dye was also included on the peptide used in the STEPL reaction. The azide-IgG conjugates shows up as green since a FAM dye was included on the peptide used in the STEPL reaction. Mixing of the ADIBO-IgG conjugate with an azide-Protein Z adapter led to a clear shift in the ADIBO-IgG band, i.e. click product (FIG. 20, lane 2). Similarly, mixing of the azide-IgG conjugate with a ADIBO-Protein Z adapter led to a clear shift in the azide-IgG band, i.e. click product (FIG. 20, lane 4). Since, ADIBO forms a covalent linkage exclusively with azide and not itself, and vice versa, only the desired IgG-protein conjugates are formed. No homodimers are formed.

Figure 21:
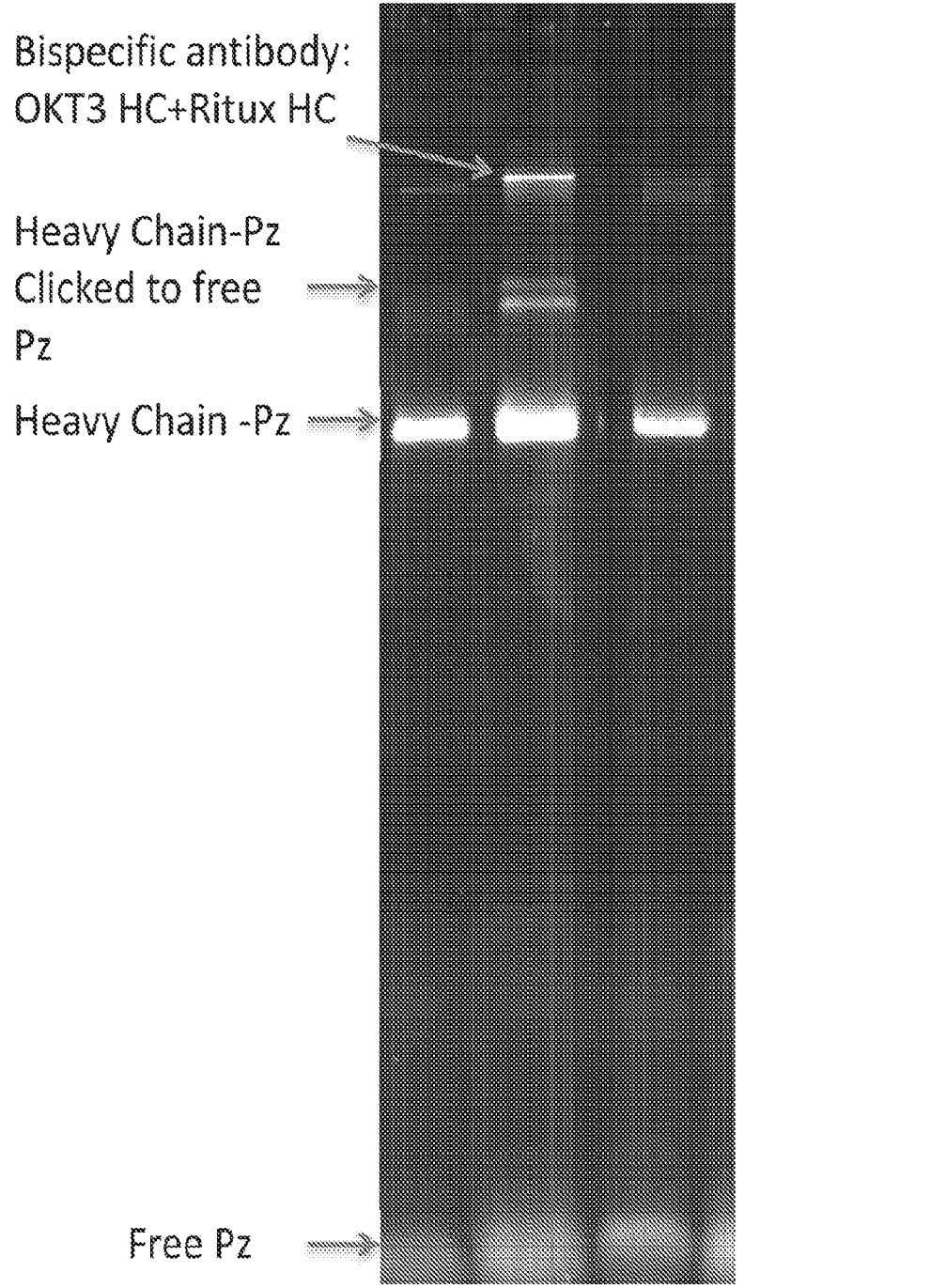
FIG. 21. Modular bispecific antibodies made using Tetrazine-TCO click chemistry. A bispecific consisting of OKT3 and Rituximab is shown.

As a second example of using chemical linking modules to form bispecific antibodies, TCO and tetrazine labeled peptides were ligated to the C-terminal end of the Protein Z adapters via STEPL (FIG. 21). The TCO- and tetrazine-labeled adapters were then photocrosslinked to OKT3 and rituximab antibodies, respectively (FIG. 21, lanes 1 and 3). Mixing of the TCO-OKT3 conjugate with the tetrazine-rituximab conjugate resulted in the specific formation of bispecific antibodies (FIG. 21, lane 2). Some antibody monomers (i.e. heavy chain-Pz) still exist as well as some IgG-Protein Z-Protein Z conjugates (i.e. heavy chain-Pz clicked to free Pz). IgG-Protein Z-Protein Z conjugates resulted from the incomplete removal of azide and ADIBO-Protein Z adapters, which were never covalently linked to IgG.

Figure 22:
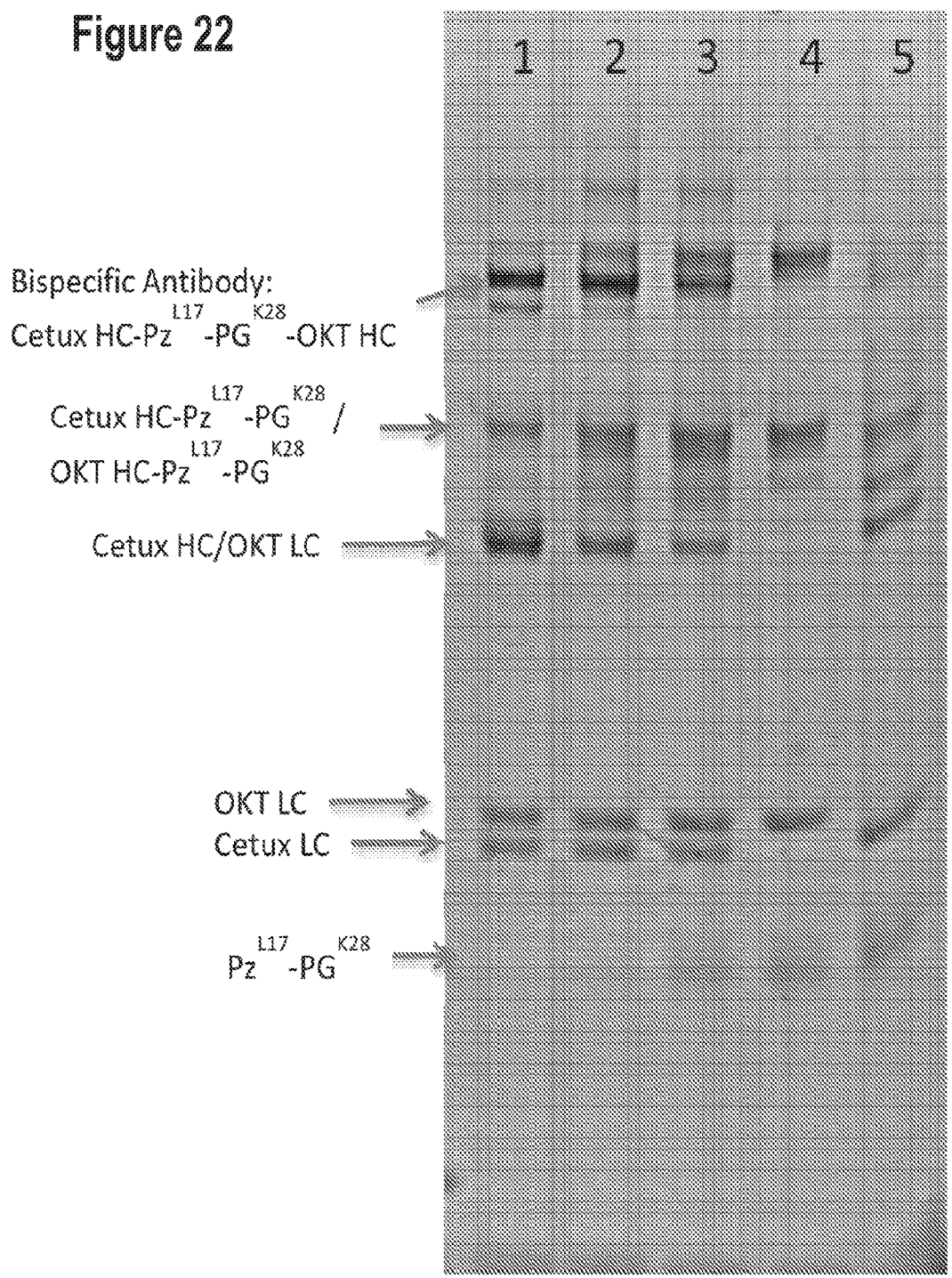
FIG. 22. A Protein Z-Protein G fusion protein with orthoganol specificity for a particular IgG subtype was made and used to make a bispecific antibody. Protein $Z^{L17}$ ($Pz^{L17}$) conjugates mIgG2a (OKT3) only. No hIgG1 (Cetux) conjugation is observed except at very high Protein $Z^{L17}$ concentrations. Protein $G^{K28}$ ($PG^{K28}$) conjugates hIgG1 (Cetux) only. No mIgG2a (OKT3) conjugation is observed except at very high Protein $G^{K28}$ concentrations. A fusion protein of Protein $Z^{L17}$-Protein $G^{K28}$ is hence "Orthogonal" and conjugates OKT3 via Protein $Z^{L17}$ and Cetux via Protein $G^{K28}$ to create the desired heterodimers between Cetux and OKT3
Figure 23:
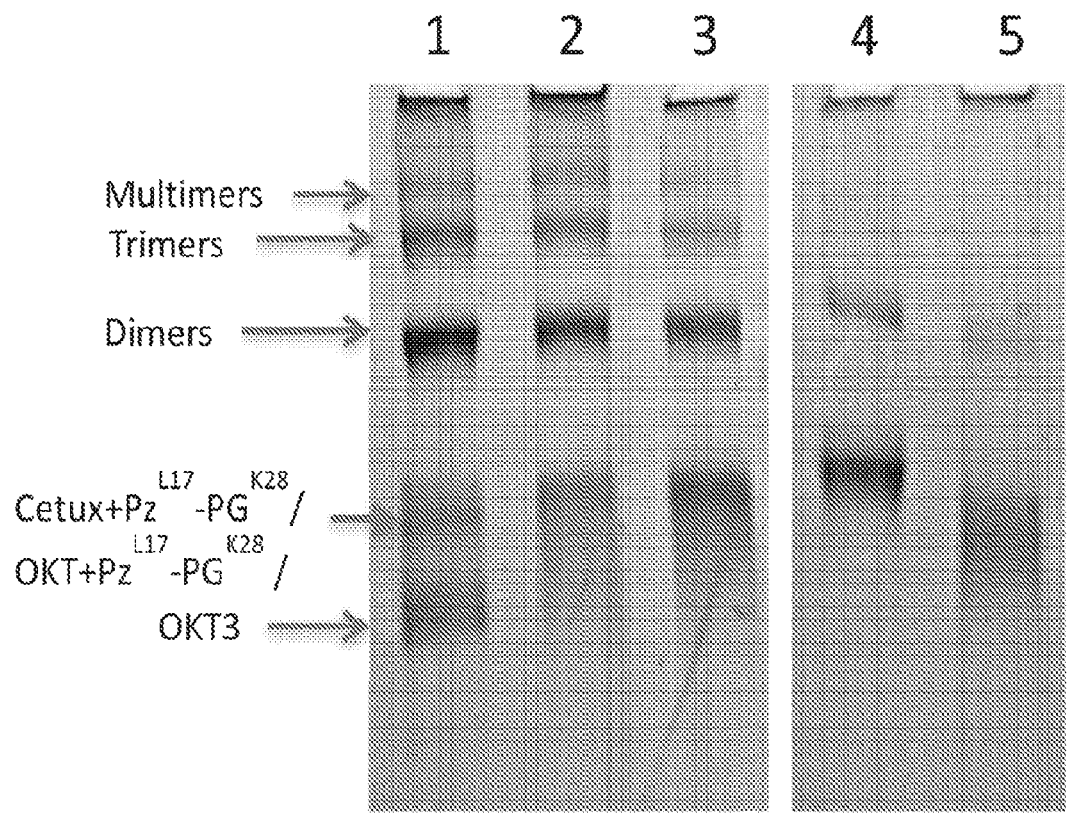
FIG. 23. $Pz^{L174}$-$PG^{K28}$ Orthogonal bispecific antibodies. Samples from FIG. 22 were analyzed via a non-reducing gel. Even at the highest Protein $Pz^{L17}$-$PG^{K28}$ concentration (Lane 4 and 5; 12 μL) only scant homodimers formed, which suggests dimers in Lanes 1-3 are mostly heterodimers.

As an alternative to using linking modules to form bispecifics, it is also possible to express a single fusion protein containing two AbBDs. While it is very straightforward to produce homodimers using this type of fusion protein, it is also possible to produce heterodimers (i.e. bispecific antibodies) if each AbBD has unique specificity for a specific IgG subtype. This was demonstrated by fusing a Protein Z adapter protein with the BPA photocrosslinker located in the L17 position ($Pz^{L17}$) to a Protein G adapter with the BPA located in the K28 position ($PG^{K28}$). $Pz^{L17}$ has unique specificity for mouse IgG2 as such as OKT3 while $PG^{K28}$ has unique specificity for human IgGs such as cetuximab. As a result, an antibody dimer is only formed when both cetuximab and OKT3 are mixed with the $Pz^{L17}$-$PG^{K28}$ fusion protein (FIGS. 22 and 23, lanes 1-3). Addition of only a single antibody, cetuximab or OKT3, results in little to no dimer formation (FIGS. 22 and 23, lanes 4 and 5).

Example 4

One-Step Production of Bispecific Antibodies:

Recently, a rapid and site-specific bioconjugation technique was developed that allows for the attachment of an anti-CD3 scFv (or any other scFv) to any full-length human IgG. Our technique relies on a small antibody-binding domain (AbBD) that is engineered to contain a photoreactive unnatural amino acid (benzoyl-phenylalanine, BPA) in its Fc-binding site (FIG. 24). The AbBD used is based on small (~6.5 kD), thermally stable domain of Protein G (HTB1). The introduction of a photoreactive amino acid allows for the formation of a covalent linkage between an scFv-AbBD fusion protein and IgG, to prevent dissociation in serum. The AbBD is capable of binding to both heavy chains of IgG (di-conjugated), thereby creating a tetravalent bispecific antibody. However, it is also possible to create a bispecific antibody with only a single scFv (i.e. trivalent/mono-conjugated). Both formats are tested. Some attributes of this approach are that it is simple, rapid (<2 hrs), efficient (100% of antibody is labeled), has no effect on antibody affinity, is amenable to high-throughput production, and either mono-conjugated or di-conjugated products are easily purified.

Mono-Conjugated Bispecific Antibodies:

According to previous reports, binding of Protein G to Fc sites of IgG does not prevent or sterically interfere with the attachment of these antibodies to the Fc receptor. Therefore, ADCC and CDC function is not expected to be lost with this bispecific antibody format. However, Protein G does prevent binding to the neonatal Fc receptor (FcRn). This leads to a half-life of 12 hours for IgG-protein G conjugates (non-crosslinked), which is much shorter than the half-life of 1 to 3 weeks for IgG. However, it is significantly longer than the half-lives of scFv's, which can be as short as 30 min.

In an attempt to maintain the long circulation half-life of native IgG, antibodies with only a single Protein G adaptor are prepared (FIG. 11), freeing up the adjacent heavy chain for FcRn binding. Mono-conjugated IgG may retain, at least partially, FcRn-mediated IgG recycling. It has been shown that FcRn binds to each site on IgG independently, with identical affinity. Circulation times can be determined. Having monovalency for CD3 is also expected to eliminate concerns over the level of cytokine release upon T cell binding. Di-conjugated bispecific antibodies are prepared and evaluated. Di-conjugated bispecific antibodies do offer the advantage of higher affinity for T cell targets and several tetravalent bispecific antibodies have entered clinical trials, including AbbVie/ABT-122, Sanofi/SAR156597, and Merrimak/MM141. The flexibility to create both mono-conjugated and di-conjugated bispecifics is a novel and valuable feature of this approach and could provide insight into designing optimal bispecific antibodies.

Figure 26:
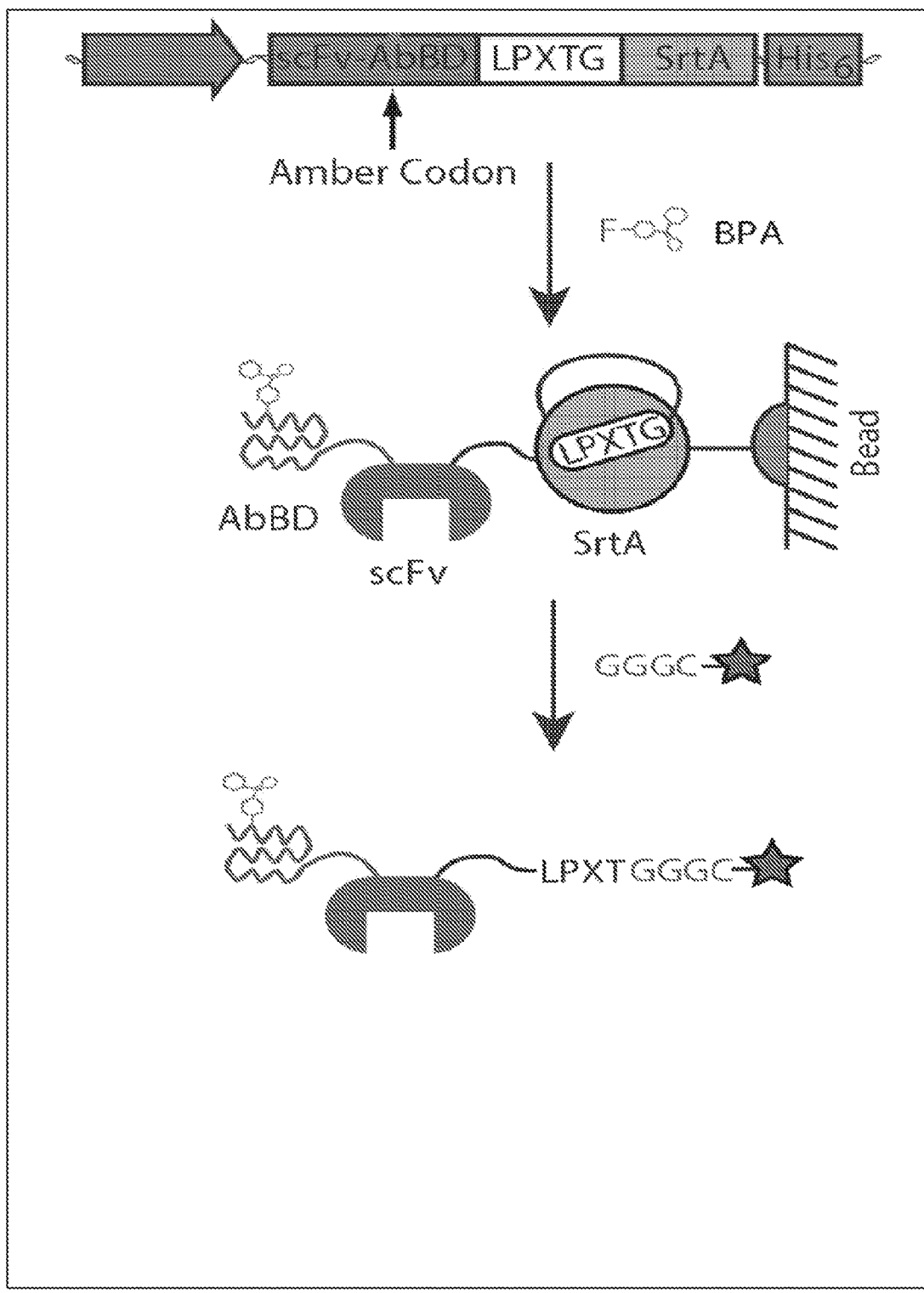
FIG. 26. Schematic describing the production of a photoreactive AbBD-scFv fusion protein with a c-terminal-modification (red star) that was introduced using sortase-tag expressed protein ligation (STEPL).

Sortase-Tag Expressed Protein Ligation (STEPL):

Recently, a technique was developed that allows the c-terminus of any single chain protein to be labeled with nearly any desirable compound, including drugs, imaging agents, biomolecules, chemical handles, haptens, polymers, nanoparticles, etc. This technique relies on Sortase A (SrtA). SrtA is a calcium-assisted transpeptidase that is responsible for anchoring surface proteins to the peptidoglycan cell wall of Gram-positive bacteria. The enzyme cleaves the peptide bond between the amino acids T and G, within the motif, LPXTG. The products remain transiently attached to SrtA, until the N-terminal glycine of another protein displaces the C-terminal fragment and forms a new peptide bond between the two-peptide chains. To take advantage of this site-specific ligation reaction, a single fusion protein construct was created that contains LPXTG, SrtA, and a His-tag, respectively, so that it can be fused to the C-terminal end of a desirable single chain protein (FIG. 26). This technique is utilized to label the anti-CD3 scFv and scFv-AbBD with a copper chelate, NOTA (1,4,7-triazacyclononane-N,N',N"-trisacetic acid) for nuclear imaging. This allows for the facile creation of a companion diagnostic without adding any additional steps to the workflow.

One advantage of the bispecific antibody production method described here is that an "off-the-shelf" full-length antibody can be used with no need for protein engineering, cloning, or other modifications. This will make bispecifics more accessible to academic labs, allowing bispecifics to be tested in a wider range and more creative applications. Moreover, since bispecific antibody production is rapid (<2 hrs) and efficient (100%). This technique is amenable to high-throughput production, which is not currently possible with any other technique. This may allow for rapid screening of bispecific antibody pairs (e.g. different targets, different epitopes, different affinities) for optimal performance. Other advantages include the ability to swap between murine and human antibodies that target the same epitope and easily add additional functionality—toxins, imaging agents, drugs, radiopharmaceuticals or other chemical modifications—via STEPL. Notably, there are many issues that can ultimately influence the clinical applicability and utility of a bispecific antibody; however, even if this approach proves to be unfit for clinical use, it is expected that the ability to rapidly and easily screen antibodies for optimal performance could still be used to guide other bispecific antibody production techniques. This is expected to hold particularly true for other tetravalent bispecific antibody formats that closely resemble the bispecific antibodies that we are creating, e.g. IgG-scFv, scFv$_2$-Fc, DVD-Ig, etc.

Figure 27:
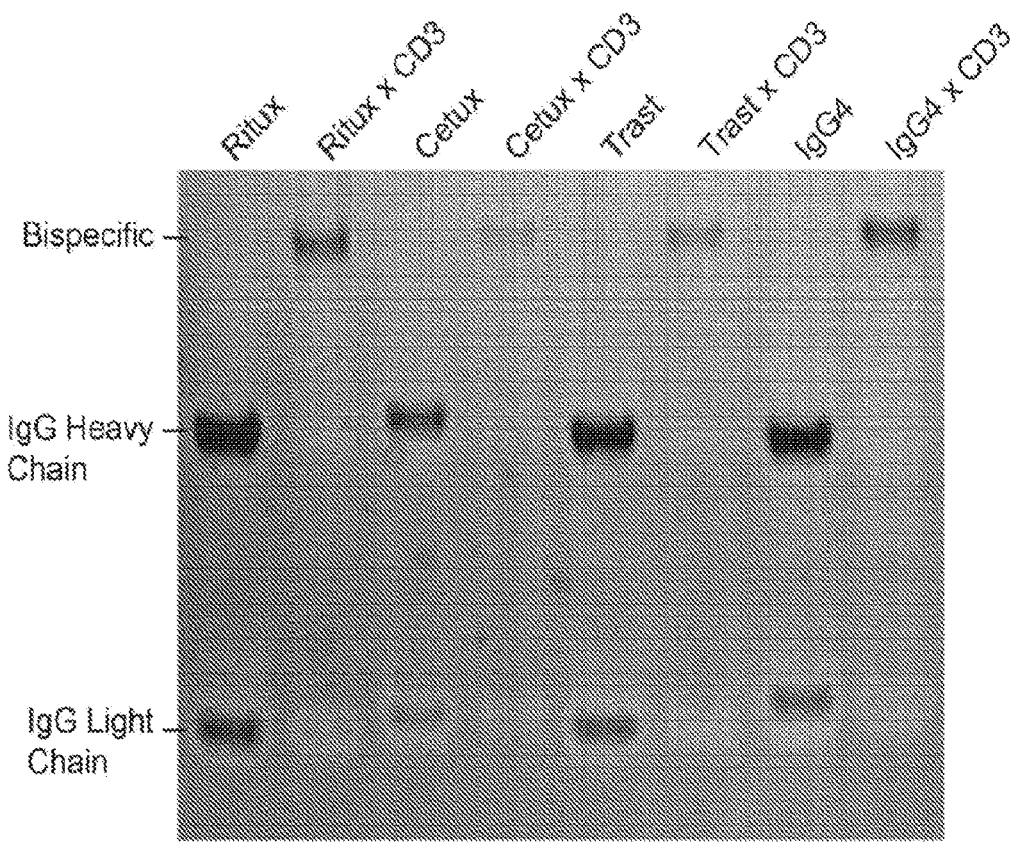
FIG. 27. Reducing SDS-PAGE of four different human antibodies—Rituximab, Cetuximab, Trastuzumab, and IgG4—alone or after photo-crosslinking with AbBD-anti-CD3 scFv. Free AbBD-scFv was efficiently removed via filtration.

Formation of Bispecific Antibodies Using AbBD-scFv Fusion Proteins:

To prepare bispecific antibodies, a photoreactive AbBD was fused to an anti-CD3 scFv (OKT3 parent antibody). To create a bispecific antibody, the expressed AbBD-scFv is simply mixed with the IgG of choice and photocrosslinked for hrs. To demonstrate the simplicity of the approach, 4 unique bispecific antibodies were created in parallel (FIG. 27). Because of the high crosslinking efficiency between the photoreactive AbBD and IgG, essentially just two species exist after the photoreaction, diconjugated IgG and free AbBD-scFv. This makes it extremely easy to obtain highly pure tetravalent bispecific antibody, since the free AbBD is easily removed using ultrafiltration spin columns (100 kDa MWCO, Millipore). If necessary, mono-conjugated IgG and unconjugated IgG can be removed using Protein A/G beads, since the AbBD sterically blocks the di-conjugated IgG from interacting with Protein A/G.

Figure 28:
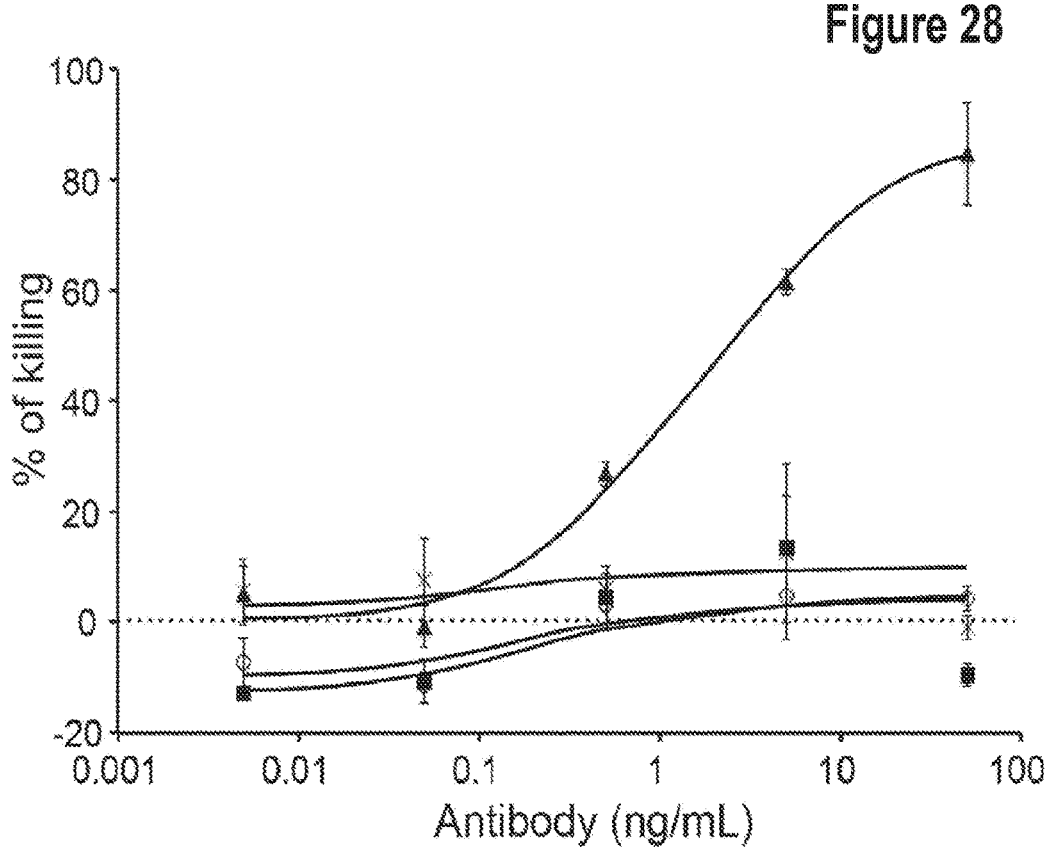
FIG. 28. T cell-mediated cell lysis assay. Di-conjugated rituximab×anti-CD3 scFv bispecific antibodies were incubated with CD20-positive Jeko B cells (▲) or CD20-negative K562 cells (○) for 24 hrs in the presence of PBMCs at an effector-to-target ratio of 10:1. Analogous studies were performed with rituximab alone (■) or rituximab+anti-CD3 scFv (x) with Jeko B cells in the presence of PBMCs at an effector-to-target ratio of 10:1. All data points are mean±SD of triplicate wells.
Figure 29:
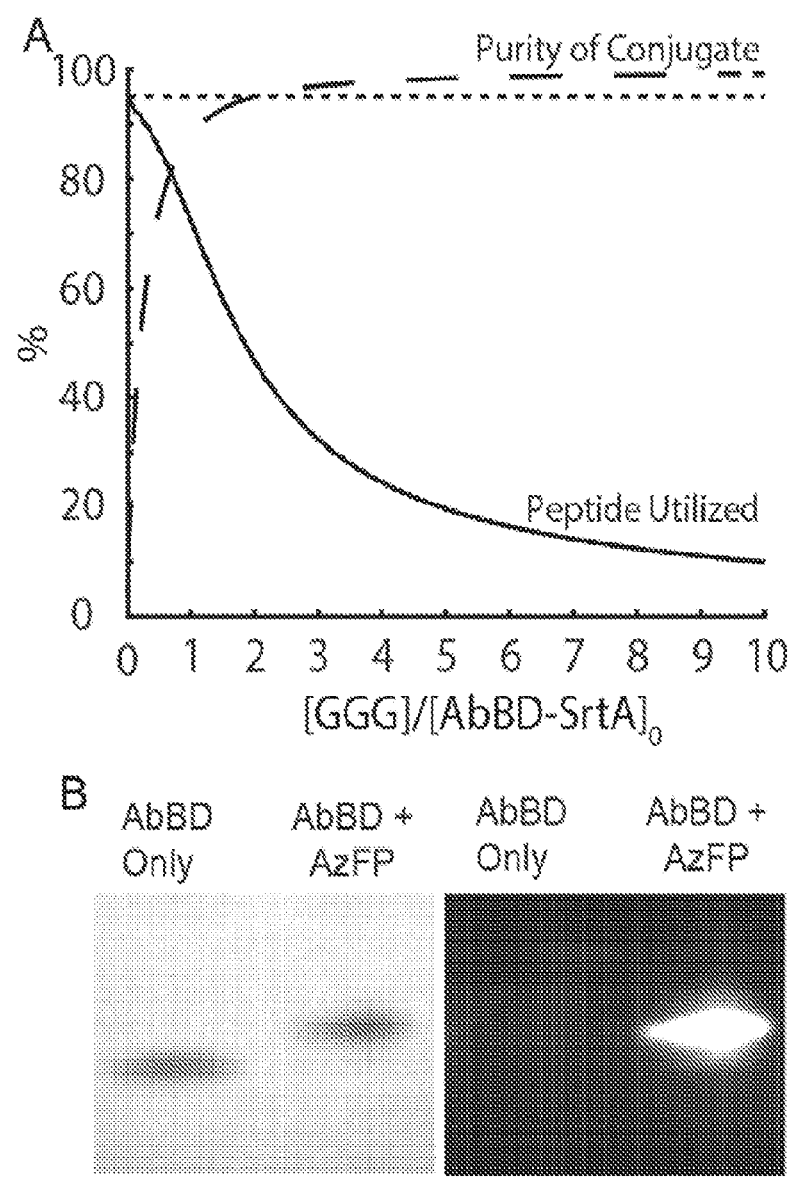
FIG. 29. (B) Plot of STEPL ligation efficiency and the % of triglycine peptide utilized, relative to the amount of expressed AbBD-SrtA. The horizontal dashed line represents 95% purity of conjugated product. (C) SDS-PAGE of unmodified AbBD and AbBD ligated to a peptide with an azide and fluorophore (AzFP). White light and fluorescent images of gel are shown.

Confirmation of Bispecific Antibody Functionality:

To demonstrate that the (di-conjugated) bispecific antibodies created using our one-step photoreaction were able to mediate cell killing, T cell-mediated cell lysis assay was performed (FIG. 28). Specifically, bispecific antibodies composed of rituximab and anti-CD3 scFv's were incubated with CD20-positive Jeko B cells. PBMCs were added at an effector-to-target ratio of 10:1 and incubated for 24 hrs. Cytotoxicity was measured via a chromium release assay. The bispecific antibody exhibited a dose-dependent cytotoxic effect with statistically significant cytotoxicity (27% lysis) measured at 0.5 ng/mL and an EC$_{50}$ of ~2 ng/mL. This is very similar to what others have observed with anti-CD20/CD3 bispecific antibodies, although direct comparisons are difficult due to cell line-to-cell line and PBMC donor-to-donor variability.

The potency of this construct is further improved by testing an alternative anti-CD3 scFv (UCHT1 parent antibody) and by varying the length of the linker between the AbBD and the scFv. Notably, no cytotoxicity was observed with CD20 negative K562 cells. Moreover, no toxicity was observed when rituximab or a mixture of anti-CD3 scFv and rituximab were incubated with Jeko B cells in the presence of PBMCs at a 10:1 effector-to-target ratio.

Figure 30:
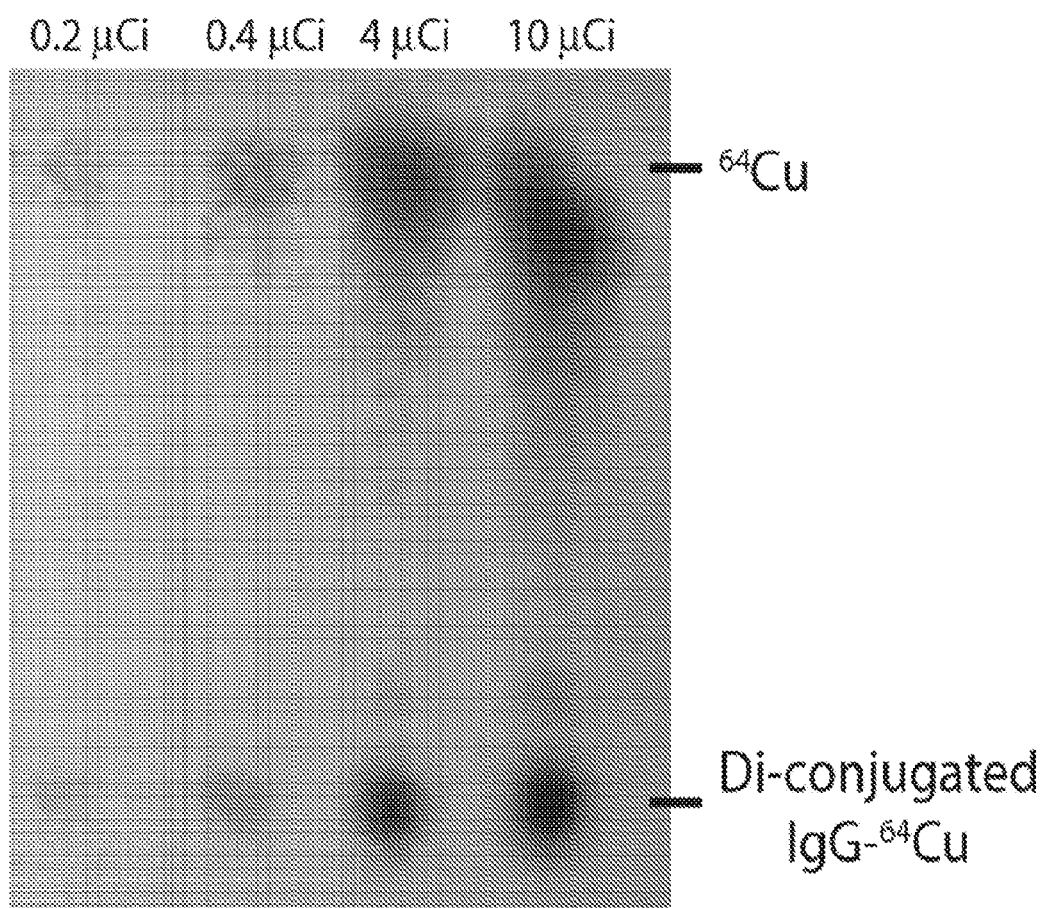
FIG. 30. TLC of di-conjugated IgG-NOTA after labeling with various amounts of $^{64}$Cu.

STEPL is utilized to label the anti-CD3 scFv and scFv-AbBD with a copper chelate, e.g., NOTA, for nuclear imaging. This allows for the facile creation of a companion diagnostic without adding any additional steps to the workflow. Data was acquired showing efficient labeling of di-conjugated IgG with Cu-64 (FIG. 30). Notably, if no additional labels are desired at the C-terminus of the AbBD-scFv, triglycine can simply be used to catalyze release from the affinity column.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An adapter comprising an antibody binding domain (AbBD) that specifically binds and crosslinks to an immunoglobulin, wherein the AbBD is a variant of a Protein G subdomain comprising an amino acid sequence with at least 90% identity to the sequence set forth in SEQ ID NO: 2 and having an amino acid replacement and/or an amino acid modification at A24, K28 or both of SEQ ID NO: 2 that is photo-reactive.

2. The adapter of claim 1, wherein the photo-reactive amino acid replacement is benzoylphenylalanine (BPA).

3. An adapter comprising an antibody binding domain (AbBD) that specifically binds and crosslinks to an immunoglobulin, wherein the AbBD is a variant of a protein G subdomain comprising the amino acid sequence as set forth in SEQ ID NO: 2 and having one or more photo-reactive non-natural amino acids that are incorporated into the AbBD, and wherein the photo-reactive amino acid is benzoylphenylalanine (BPA).

4. The adapter of claim 3, wherein the BPA replaces A24 or K28 of SEQ ID NO: 2.

5. The adapter of claim 1, wherein a cysteine is engineered into the AbBD and is modified with a photo-reactive moiety.

6. The adapter according to claim 1, wherein said AbBD further comprises a recognition motif for expressed protein ligation (EPL).

7. A conjugate composition comprising the adapter of claim 1, wherein the adapter is conjugated to a protein, a targeting agent of interest, an oligonucleotide, a DNA, an RNA, a detectable label, an imaging agent, a drug, a toxin, a hapten, a chelate, a polymer, a chemical handle, or a combination thereof.

8. The conjugate composition of claim 7, wherein the chemical handle is a click chemistry group selected from the group consisting of an azide, an alkyne, a constrained alkyne, dibenzocyclooctyne, a tetrazine, and a transcyclooctyne.

9. A fusion protein comprising the adapter of claim 1 fused in frame with an additional amino acid, a peptide or a protein.

10. The fusion protein of claim 9, wherein the additional amino acid, peptide, or protein is selected from the group consisting of SpyTag, SpyCatcher, one half of a split intein, an intent, a cysteine, an N-terminal glycine, and a sortase recognition motif.

11. The fusion protein of claim 9, wherein the AbBD is fused in frame with a fluorescent protein, a β-galactosidase, a chloramphenicol acetyl transferase, or a luciferase.

12. The fusion protein according to claim 9, further comprising an affinity tag.

13. The fusion protein according to claim 9, further comprising a recognition motif for expressed protein ligation (EPL).

14. The fusion protein of claim 9 wherein said fusion protein is conjugated to a or protein, a targeting agent of interest, an oligonucleotide, a DNA, an RNA, a detectable label, an imaging agent, a drug, a toxin, a hapten, a chelate, a polymer, a chemical handle, or a combination thereof.

15. The fusion protein of claim 14, wherein the chemical handle is a click chemistry group selected from the group consisting of an azide, an alkyne, a constrained alkyne, dibenzocyclooctyne, a tetrazine, and a transcyclooctyne.

16. The fusion protein of claim 9, wherein said additional amino acid, peptide, or protein is a targeting ligand, an antibody, or an antibody fragment.

17. A conjugate composition comprising the adapter of claim 1 operably linked to an immunoglobulin Fc region.

18. The conjugate composition of claim 17, wherein the immunoglobulin is an IgG molecule.

* * * * *